(12) United States Patent
Uemura et al.

(10) Patent No.: US 12,085,560 B2
(45) Date of Patent: Sep. 10, 2024

(54) BIOCHEMICAL REACTION SUBSTRATE WITH SLOPING FLOW PASSAGE TO ABSORBER AND ANALYZER THEREFORE

(71) Applicants: NIPPON CHEMIPHAR CO., LTD., Tokyo (JP); UEDA JAPAN RADIO CO., LTD., Ueda (JP)

(72) Inventors: Kenji Uemura, Misato (JP); Norio Tanimoto, Misato (JP); Mai Egami, Misato (JP); Takahiro Mataki, Tokyo (JP); Yumi Konishi, Misato (JP); Motoe Shimizu, Ueda (JP); Shigenori Takahashi, Ueda (JP); Koji Sakaguchi, Ueda (JP)

(73) Assignee: NIPPON CHEMIPHAR CO., LTD., Tokyo (JP)

( * ) Notice: Subject to any disclaimer, the term of this patent is extended or adjusted under 35 U.S.C. 154(b) by 991 days.

(21) Appl. No.: 16/966,765

(22) PCT Filed: Feb. 1, 2019

(86) PCT No.: PCT/JP2019/003559
§ 371 (c)(1),
(2) Date: Jul. 31, 2020

(87) PCT Pub. No.: WO2019/151468
PCT Pub. Date: Aug. 8, 2019

(65) Prior Publication Data
US 2021/0364503 A1    Nov. 25, 2021

(30) Foreign Application Priority Data

Feb. 2, 2018  (JP) ................................. 2018-017628
Oct. 1, 2018  (JP) ................................. 2018-186756

(51) Int. Cl.
*G01N 33/543*  (2006.01)
*B01L 3/00*   (2006.01)
(Continued)

(52) U.S. Cl.
CPC ............ *G01N 33/543* (2013.01); *B01L 3/502* (2013.01); *B01L 9/527* (2013.01); *G01N 35/00732* (2013.01); *G01N 35/021* (2013.01)

(58) Field of Classification Search
CPC .......... G01N 33/543; G01N 35/00732; G01N 35/021; G01N 33/558; G01N 33/54366;
(Continued)

(56) References Cited

U.S. PATENT DOCUMENTS 3,690,836 A  *  9/1972  Buissiere ................. C12Q 1/04
                                              435/287.7
3,697,227 A  *  10/1972  Agnew .................. B01L 3/502
                                              422/409
(Continued)

FOREIGN PATENT DOCUMENTS

CN    101124483 A    2/2008
JP    03-154853 A    7/1991
(Continued)

OTHER PUBLICATIONS

International Search Report for PCT/JP2019/003559 dated May 14, 2019 (PCT/ISA/210).
(Continued)

*Primary Examiner* — Arlen Soderquist
(74) *Attorney, Agent, or Firm* — Sughrue Mion, PLLC

(57) ABSTRACT

Provided is a biochemical reaction substrate which can achieve higher test sensitivity and shorter testing time in an allergy test, which can also reduce a required amount of blood or the like needed as a specimen and decrease the number of test steps, thereby facilitating performance of the
(Continued)

test, and which is to be used in an allergy test in which infection risk of the test staff is reduced. A biochemical reaction substrate, including: a reaction plate; an absorber; a reaction plate storing portion for storing the reaction plate; an absorber storing portion for storing the absorber; a storage container having a heated portion; and a cover assembled to the storage container so as to cover at least a part of the reaction plate and the absorber stored in the storage container, wherein the reaction plate includes a reaction area in which a specific binding substance that specifically reacts with a substance to be tested in a specimen is immobilized, and a flow passage that connects the absorber and the reaction area, and wherein the cover includes an injection hole for injecting a specimen or the like into the reaction plate.

12 Claims, 27 Drawing Sheets

(51) Int. Cl.
  *B01L 9/00* (2006.01)
  *G01N 35/00* (2006.01)
  *G01N 35/02* (2006.01)
(58) Field of Classification Search
  CPC ............... G01N 35/02; G01N 35/1002; G01N 2035/0436; G01N 2035/00524; Y10S 436/81; B01L 3/502; B01L 9/527
  USPC .............. 436/43, 46–48, 164–165, 169, 172; 422/401–404, 408, 411–413, 420–430, 422/63–65, 67
  See application file for complete search history.

(56) References Cited

U.S. PATENT DOCUMENTS

| | | | | |
|---|---|---|---|---|
| 4,076,592 A * | 2/1978 | Bradley | C12M 41/36 | 435/288.5 |
| 4,113,436 A * | 9/1978 | Werder | G01N 35/021 | 436/98 |
| 4,246,339 A * | 1/1981 | Cole | G01N 33/54366 | 422/534 |
| 4,623,461 A * | 11/1986 | Hossom | C12M 41/46 | D23/209 |
| 4,844,868 A * | 7/1989 | Rokugawa | G01N 35/1002 | 422/65 |
| 4,857,453 A * | 8/1989 | Ullman | G01N 33/54386 | 436/514 |
| 4,916,056 A * | 4/1990 | Brown, III | G01N 33/528 | 435/287.7 |
| 4,918,025 A * | 4/1990 | Grenner | G01N 33/5302 | 436/807 |
| 4,943,522 A * | 7/1990 | Eisinger | G01N 33/54386 | 436/514 |
| 4,944,924 A * | 7/1990 | Mawhirt | B01L 9/06 | 422/65 |
| 4,956,302 A * | 9/1990 | Gordon | G01N 33/558 | 436/162 |
| 4,981,785 A * | 1/1991 | Nayak | G01N 33/558 | 436/514 |
| 4,981,786 A * | 1/1991 | Dafforn | G01N 33/558 | 436/514 |
| 5,075,077 A * | 12/1991 | Durley, III | B01L 3/545 | 435/805 |
| 5,075,078 A * | 12/1991 | Osikowicz | G01N 33/54388 | D24/223 |
| 5,137,808 A * | 8/1992 | Ullman | G01N 33/54386 | 436/514 |
| 5,147,609 A * | 9/1992 | Grenner | B01L 3/5023 | 435/7.1 |
| 5,176,880 A * | 1/1993 | Iwasaki | B01L 3/545 | 422/65 |
| 5,209,904 A * | 5/1993 | Forney | G01N 33/5302 | 359/398 |
| 5,223,220 A * | 6/1993 | Fan | G01N 33/5302 | 435/805 |
| 5,244,630 A * | 9/1993 | Khalil | G01N 35/1002 | 422/414 |
| 5,275,785 A * | 1/1994 | May | G01N 33/558 | 436/514 |
| 5,281,540 A * | 1/1994 | Merkh | G01N 35/00029 | 422/547 |
| 5,320,808 A * | 6/1994 | Holen | G01N 35/025 | 422/68.1 |
| 5,384,264 A * | 1/1995 | Chen | G01N 33/54366 | 436/805 |
| 5,580,790 A * | 12/1996 | Wall | G01N 21/07 | 422/562 |
| 5,939,331 A * | 8/1999 | Burd | G01N 33/80 | 436/535 |
| 5,962,336 A * | 10/1999 | Sun | G01N 33/54366 | 436/805 |
| 5,988,857 A | 11/1999 | Ozawa et al. | | |
| 6,235,539 B1 * | 5/2001 | Carpenter | G01N 33/558 | 435/7.1 |
| 6,338,969 B1 * | 1/2002 | Shareef | G01N 33/558 | 422/412 |
| 7,189,522 B2 * | 3/2007 | Esfandiari | G01N 33/56988 | 435/7.1 |
| 7,387,890 B2 * | 6/2008 | Esfandiari | G01N 33/558 | 436/514 |
| 8,663,578 B2 * | 3/2014 | Sukawa | G01N 33/491 | 422/503 |
| 2002/0019062 A1 * | 2/2002 | Lea | B01L 3/502753 | 435/287.2 |
| 2002/0127142 A1 | 9/2002 | Ishihara et al. | | |
| 2004/0022682 A1 * | 2/2004 | Itoh | G01N 35/04 | 422/65 |
| 2004/0115832 A1 * | 6/2004 | Shareef | B01L 3/5023 | 436/514 |
| 2005/0250173 A1 | 11/2005 | Davis et al. | | |
| 2006/0216199 A1 * | 9/2006 | Koike | G01N 35/026 | 422/65 |
| 2008/0269075 A1 | 10/2008 | Lea et al. | | |
| 2010/0239459 A1 * | 9/2010 | Alajem | G01N 33/5306 | 422/430 |

FOREIGN PATENT DOCUMENTS

| | | |
|---|---|---|
| JP | 10-062426 A | 3/1998 |
| JP | 2000-275258 A | 10/2000 |
| JP | 2001-235471 A | 8/2001 |
| JP | 2001-349896 A | 12/2001 |
| JP | 2004-061160 A | 2/2004 |
| JP | 2007-24549 A | 2/2007 |
| JP | 2007-536558 A | 12/2007 |
| JP | 2008-014638 A | 1/2008 |
| JP | 2011-13000 A | 1/2011 |
| JP | 2011-133285 A | 7/2011 |
| JP | 2013-140176 A | 7/2013 |
| JP | 2016-24054 A | 2/2016 |
| JP | 2016-200431 A | 12/2016 |
| LU | 100411 B1 | 12/2017 |
| WO | 02/093169 A1 | 11/2002 |
| WO | 2016/163494 A1 | 10/2016 |

OTHER PUBLICATIONS

Extended European Search Report dated Oct. 4, 2021 from the European Patent Office in European Application No. 19747069.3.

* cited by examiner

BIOCHEMICAL REACTION SUBSTRATE WITH SLOPING FLOW PASSAGE TO ABSORBER AND ANALYZER THEREFORE

TECHNICAL FIELD

The present invention relates to a biochemical reaction substrate for measuring an amount of a specimen material having physiological activity based on a biochemical reaction treatment such as an immunoassay method, and an analyzer for analyzing a reaction between a specimen such as blood and a reagent, and particularly to an analyzer that can achieve downsizing of the analyzer, reduction of the testing time, reduction of the amount of specimen, and reduction of testing cost.

BACKGROUND ART

Testing of biological substances for testing the presence or amount of a substance in the body is important for knowing a health condition and determining a treatment method. Further, testing of a biological substance requires performing many kinds of tests in the present age where living environments are diversified, and thus there are needs of achieving higher speed and higher sensitivity of such testing. For example, in the treatment of allergic diseases, it is important to first understand the allergic diseases that the patient is suffering from. This is because there are various causes of allergies in recent years, and it is necessary to identify the cause in order to receive proper treatment such as one using a proper drug.

Various methods are known as such an allergy test method, and for example, as described in Patent Literature 1, a method for quantifying the IgE antibody against a specific allergen in a blood sample collected from a subject by solid phase sandwich immunoassay is generally used. In this method, for example, a solid-phase carrier such as a glass filter on which a ligand-capturing antibody is adsorbed, and a protein adsorption site other than the ligand-capturing antibody adsorption site is sealed with a blocking agent such as casein is prepared, and on one hand, a ligand to which a specific allergen such as mite or pollen is bound is prepared, and this is mixed with a blood sample to form a complex between the specific allergen bound to a ligand and an IgE antibody against the specific allergen in the blood sample. Then, the mixed solution containing this complex is added to the above-described solid-phase carrier having a ligand-capturing antibody adsorbed thereon, to bind a part of one ligand in the complex to the ligand-capturing antibody, and then an anti-IgE antibody labeled with an enzyme or the like is added, and the part of the IgE antibody in the complex is bound to the labeled anti-IgE antibody. Next, excessive labeled anti-IgE antibody that has not bound to the complex is removed, and a coloration reaction depending on the type of label is performed to detect the labeled anti-IgE antibody bound to the IgE antibody. The obtained detection result is compared with a calibration curve prepared in advance using a standard IgE antibody to quantify the IgE antibody with respect to the specific allergen in the blood sample.

To perform the above described test, there is known a testing method by use of a biological reaction substrate in which one specific allergen is bound to a porous filter of the one biological reaction substrate, and an apparatus therefor. Moreover, as the biological reaction substrate, it is possible to use a reaction container for immunological measurement, which uses a glass fiber having an appropriate physical strength in the lower part of a porous filter (solid phase carrier), and combines, in the lower part thereof, an absorbing layer composed of cellulose for absorbing the solution which has passed through the solid phase carrier (see Patent Literature 2).

Similarly, as described in Patent Literature 3, a biochip analysis method capable of automating the reaction detection process between specimens and antigens and rapidly obtaining measurement results after the specimen is collected using a biochip in which antigens of various allergens are mounted as independent spots, that is, spaced spots, the specimen and the antigen are collected is disclosed.

Similarly, as described in Patent Literature 4, a method of removing a cleaning solution and the like without using a suction nozzle while using a biochip on which antigens of various allergens are mounted as independent spots, that is, spaced spots, is disclosed.

Further, conventionally, various types of analyzers have been known as the analyzer for analyzing the reaction between a specimen such as blood and a reagent, and for example, an analyzer as shown in Patent Literature 5 is known. The analyzer described in Patent Literature 5 includes: one or more test cartridges each including at least a specimen cell storing a specimen, a reagent cell storing a reagent, and a reaction cell in which the specimen and the reagent are caused to react, and having a form in which each cell is arranged linearly; an apparatus housing having a space portion inside for a predetermined set stage and a test stage adjacent to the set stage; a cartridge holding device provided on the set stage and having a cartridge receiving portion for holding the one or more test cartridges; a cartridge conveying device provided in the test stage and for carrying-in the test cartridge held by the cartridge holding device linearly into the test stage, and carrying-out the test cartridge along a longitudinal direction along the arrangement direction of each cell of carried-in test cartridges in the test stage linearly, while carrying-out the test cartridge after test from the test stage to the set stage linearly, thereby returning it to a cartridge receiving portion of the cartridge holding device; a specimen reagent dispensing device provided corresponding to a dispensing position preset in a part of a conveying path of the test cartridge in the test stage, and for dispensing a specimen and a reagent of the concerned test cartridge to a reaction cell for the test cartridge in a state in which a target cell for dispensing of the test cartridge in the test stage, which has been carried-in by the cartridge conveying device is conveyed to the dispensing position of being conveyed and arranged at a dispensing position; a measuring device provided corresponding to a measurement position preset in a part of the conveyance path of the test cartridge in the test stage, and for measuring the reaction between a specimen and a reagent in a reaction cell, which are dispensed by the specimen reagent dispensing device, in a state in which the reaction cell of the test cartridge in the test stage, which has been conveyed by the cartridge conveying device, is conveyed to and disposed at the measurement position; a constant temperature bath which is heated by a heating source and keeps the liquid temperature in at least the reaction cell of the test cartridge in the test stage, which has been conveyed by the cartridge conveying device, at a preset constant environmental temperature; and a constant-temperature bath control device having a temperature detector capable of detecting internal environmental temperature of the test stage, and for controlling a set temperature of the heating source based on the internal environmental temperature detected by the temperature detector such that when the internal environmental temperature is lower than a predetermined threshold value, the set temperature of the heating source of the constant temperature bath is raised higher than when the internal environmental temperature is equal to or higher than the threshold value.

According to such an analyzer, since there is provided a constant temperature bath for keeping the liquid temperature in the reaction cell of the test cartridge at a preset constant environmental temperature after a specimen and a reagent are dispensed into the reaction cell of the test cartridge, it is possible to effectively prevent deterioration in the measurement accuracy associated with changes in the test cartridge and the environmental temperature.

CITATION LIST

Patent Literature

Patent Literature 1
Japanese Patent Laid-Open No. 2011-133285
Patent Literature 2
Japanese Patent Laid-Open No. 2001-235471
Patent Literature 3
Japanese Patent Laid-Open No. 2011-13000
Patent Literature 4
International Publication No. 2016/163494
Patent Literature 5
Japanese Patent Laid-Open No. 2016-24054

SUMMARY OF INVENTION

Technical Problem

However, as described in Patent Literature 2, in a test method and an apparatus by use of a reaction container, although measurement can be performed in a relatively short period of time, such as 12 minutes for measuring one specimen, and about 39 minutes for measuring 90 specimens, it is necessary to prepare a specimen (such as blood) for each specific allergen so that a large amount of specimen is required. Therefore, in cases of infants, it may have been difficult to secure specimens necessary for measurement.

Moreover, the art described in Patent Literature 3 requires a suction nozzle for sucking each liquid supplied from each nozzle such as a cleaning nozzle, an antibody nozzle, and a reagent nozzle so that it takes time until completing suction of each liquid, and there is a risk that extraneous matter adhered to the suction nozzle adheres to the biochip, causing contamination.

Moreover, in the art described in Patent Literature 4, while a labeled anti-IgE antibody is detected by performing a coloration reaction after causing an IgE antibody against a specific allergen, which specifically binds to antigens of various allergens immobilized on the second base portion, to bind to an anti-IgE antibody labeled with an enzyme or the like (labeled anti-IgE antibody), since the first base portion and the cover member are laminated on the upper part of the second base portion, it cannot be an effective method for detecting a reaction with a weak degree of coloration and detection at high sensitivity may not be possible.

As described above, in conventional allergy tests, higher test sensitivity and shorter testing time are desired, and since a large amount of blood or the like to be used as a specimen is required, reduction of the amount of specimen is also desired. Moreover, in an allergy test, it has been an issue to reduce the number of steps in a reaction operation to save the labor of the test staff, and, because the blood of the patient is handled as a specimen, it is required to reduce the risk of infection by a disease from which the patient is suffering.

Further, in the analyzer described in Patent Literature 5, while after the specimen or the reagent is dispensed into the reaction cell, a predetermined amount of the specimen or the reagent is sucked and held, and after the test cartridge having the reaction cell is conveyed to the measurement position, the predetermined specimen and the reagent are ejected into the reaction cell to be measured to perform the test, such a method of sucking the specimen or the reagent has a problem that the apparatus becomes large sized, and the manufacturing cost of the apparatus also increases.

Further, although a method is known in which, to reduce the testing time, a specimen and a reagent are dispensed into a reaction cell, thereafter stirring the reaction cell, and then excessive specimen and reagent are drained, providing such stirring and drainage mechanisms causes problems such as increase in size of the analyzer and increase in manufacturing cost.

Accordingly, the present invention has been made to solve such problems and has its object to provide a biochemical reaction substrate which can achieve higher test sensitivity and shorter testing time in an allergy test, which can also reduce a required amount of blood or the like to be used as a specimen and decrease the number of test steps, thereby facilitating performance of the test, and which is to be used in an allergy test in which an infection risk of the test staff is reduced.

Further, the present invention has been made to solve such problems and has its object to provide an analyzer which enables downsizing of the analyzer and suppression of production cost thereof even when mechanisms of stirring and drainage of the reaction cell are added to reduce the testing time.

Solution to Problem

A biochemical reaction substrate according to the present invention to solve the above described problem includes: a reaction plate; an absorber; a reaction plate storing portion for storing the reaction plate; an absorber storing portion for storing the absorber; a storage container having a heated portion; and a cover assembled to the storage container so as to cover at least a part of the reaction plate and the absorber stored in the storage container, wherein the reaction plate includes a reaction area in which a specific binding substance that specifically reacts with a substance to be tested in a specimen is immobilized, and a flow passage that connects the absorber with the reaction area, and wherein the cover includes an injection hole for injecting the specimen or the like into the reaction plate.

Further, in the biochemical reaction substrate according to the present invention, it is preferable that the reaction plate is formed by a flow-out prevention wall to be continuous with the flow passage, the flow-out prevention wall being formed in such a way as to surround the reaction area.

Further, in the biochemical reaction substrate according to the present invention, it is preferable that the cover includes an inner wall portion abutting the reaction plate along at least a part of the outer peripheral edge of the flow-out prevention wall.

Further, in the biochemical reaction substrate according to the present invention, it is preferable that the inner wall portion has a missing portion for suction prevention formed at a position close to the flow passage, and the reaction plate storing portion has a storage portion groove formed to be continuous with the absorber storing portion.

The analyzer according to the present invention for solving the above described problems is an analyzer for analyzing reaction between a specimen and a reagent, the analyzer comprising: an installation area where a reagent cartridge for storing the specimen and the reagent, and a chip device for dispensing the specimen and the reagent are installed; a dispensing area where the specimen and the reagent is dispensed into the chip device; a stirring area where the dispensed specimen and/or the reagent is stirred and mixed; a drainage area where the stirred and mixed specimen and/or reagent are drained; and a detection area where reaction between the specimen and the reagent in the chip device substrate is detected, wherein the installation area, the dispensing area, the stirring area, the drainage area and the detection area are arranged on a same straight line.

Further, the analyzer according to the present invention preferably includes a guide device disposed along the same straight line and a moving table guided by the guide device.

Further, in the analyzer according to the present invention, it is preferable that the installation area and the drainage area are each disposed at either end portion of the same straight line.

Further, in the analyzer according to the present invention, it is preferable that the stirring area is oscillated by reciprocally moving the moving table along the same straight line.

Further, in the analyzer according to the present invention, it is preferable that the dispensing area includes a dispensing nozzle which is movable in a direction substantially perpendicular to the same straight line.

Further, in the analyzer according to the present invention, it is preferable that the drainage area includes a tilting mechanism which includes a stopper formed at an end portion of the same straight line, and causes the chip device to abut against the stopper and to be tilted.

Further, in the analyzer according to the present invention, it is preferable that the detection area includes a light shielding portion for shielding the chip device from light, and a detection camera for detecting the chip device surface, and that the detection camera includes a moving mechanism that allows the detection camera to move in a direction substantially perpendicular to the same straight line.

Further, in the analyzer according to the present invention, it is preferable that the light shielding portion includes an adjustment mechanism that is moved along with the detection camera by the moving mechanism, and can adjust the distance of the end portion of the light shielding portion from the detection camera.

Further, in the analyzer according to the present invention, it is preferable that the adjustment mechanism includes a first cylinder at one end of which the detection camera is attached, and a second cylinder to be assembled to the first cylinder.

Advantageous Effects of Invention

According to the present invention, since the reaction plate has a reaction area in which a specific binding substance (for example, an antigen (allergen)) that specifically reacts with the substance to be tested in the specimen is immobilized and a flow passage that connects the absorber and the reaction area, and the cover has an injection hole for injecting a specimen or the like into the reaction plate, the number of testing steps can be reduced (for example, since the cleaning solution is drained, the number of steps to absorb the cleaning solution from the reaction area is omitted) and the test can be easily performed. Moreover, since an allergy test can be performed without the test staff directly contacting the blood or the like to be used as the specimen, it is possible to reduce the risk of infection of test staff.

Moreover, since reaction between many types of allergens and antigens can be detected in the reaction area, it is possible to reduce a required amount of blood or the like to be used as a specimen.

Furthermore, according to the present invention, since the installation area, the dispensing area, the stirring area, the drainage area, and the detection area are arranged on the same straight line, it is possible to achieve downsizing of the analyzer even when the testing time is reduced by performing stirring and drainage of the chip device into which the specimen and the reagent are dispensed.

DESCRIPTION OF EMBODIMENTS

Hereinafter, a biochemical reaction substrate and an analyzer according to the present invention will be described with reference to the drawings. It should be noted that the following embodiments do not limit the invention according to each claim, and all the combinations of the features described in the embodiments are not necessarily essential to the solution of the invention.

Figure 1:
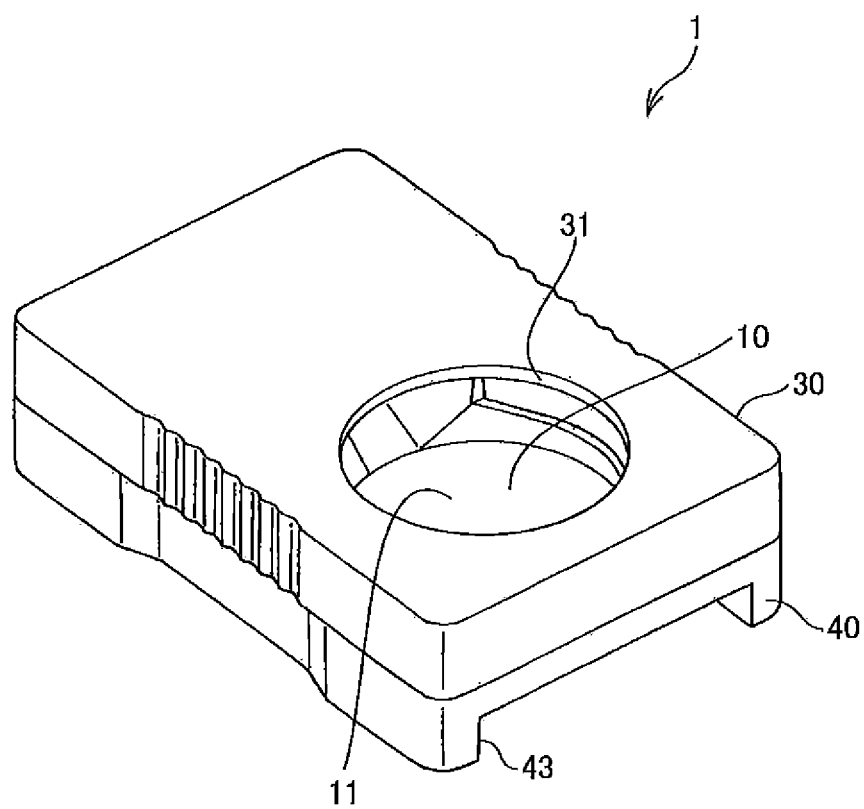
FIG. 1 is a perspective view of a biochemical reaction substrate according to an embodiment of the present invention.
Figure 2:
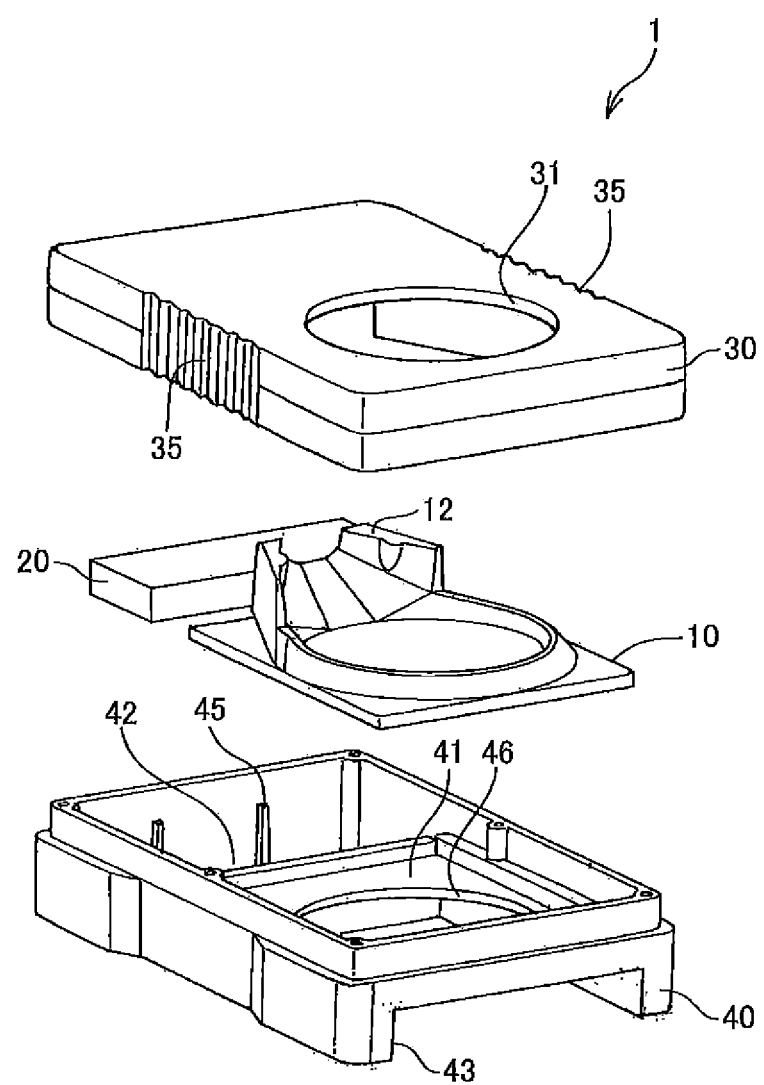
FIG. 2 is an exploded view of a biochemical reaction substrate according to an embodiment of the present invention.
Figure 3:
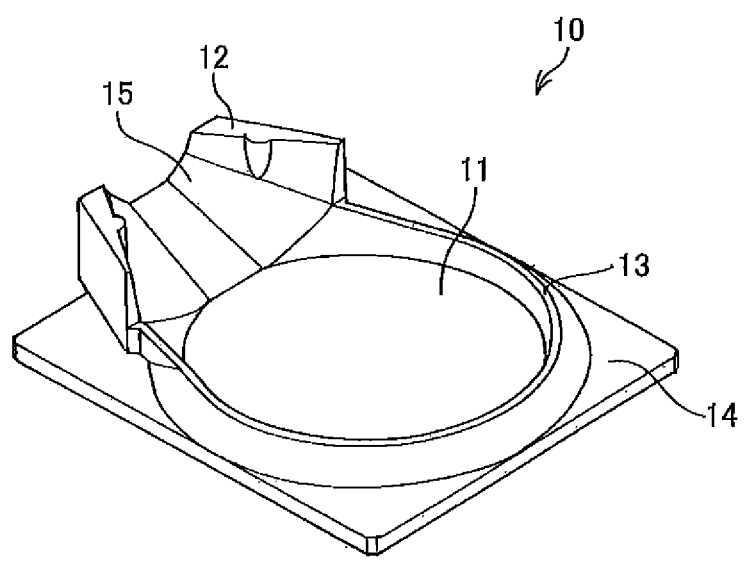
FIG. 3 is a perspective view of a reaction plate to be used for a biochemical reaction substrate according to an embodiment of the present invention.
Figure 4:
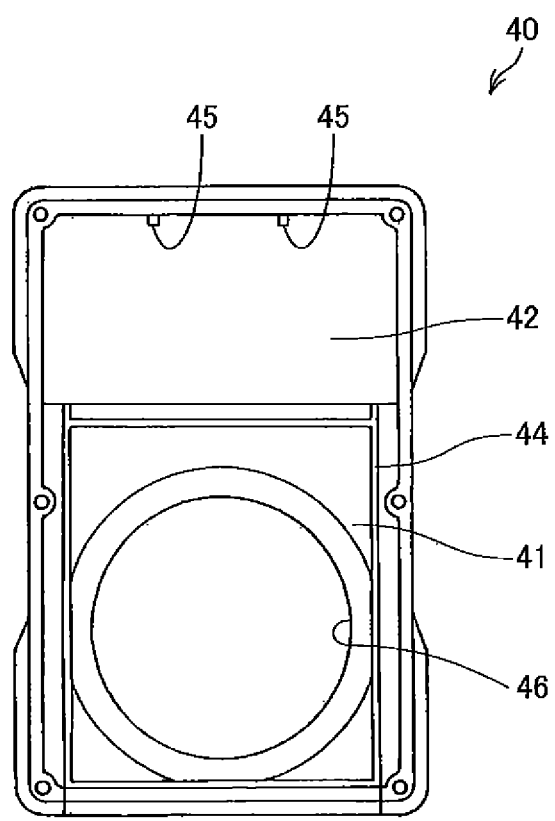
FIG. 4 is a top view of a storage container to be used for a biochemical reaction substrate according to an embodiment of the present invention.
Figure 5:
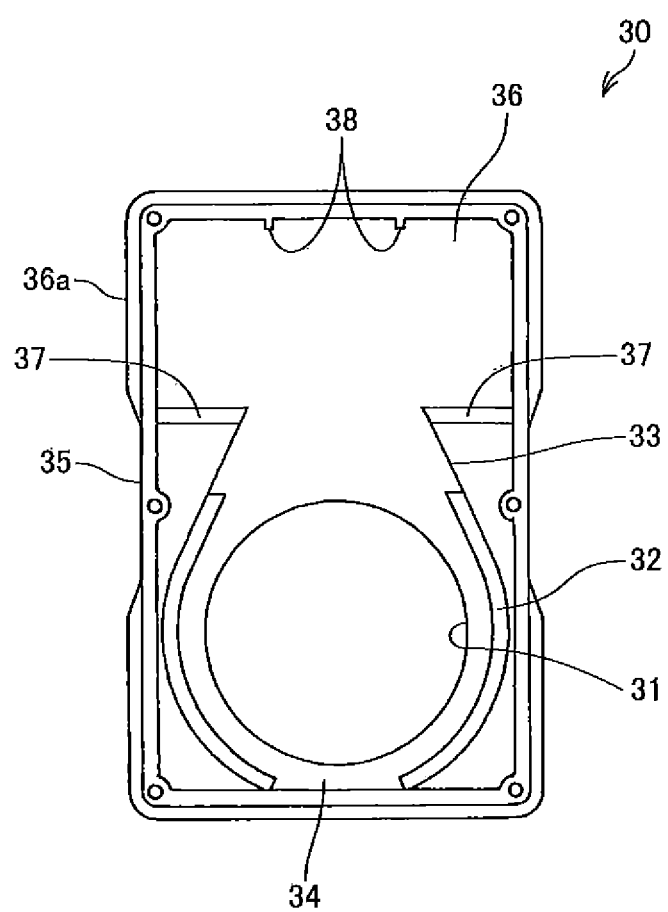
FIG. 5 is a bottom view of a cover to be used for a biochemical reaction substrate according to an embodiment of the present invention.
Figure 6:
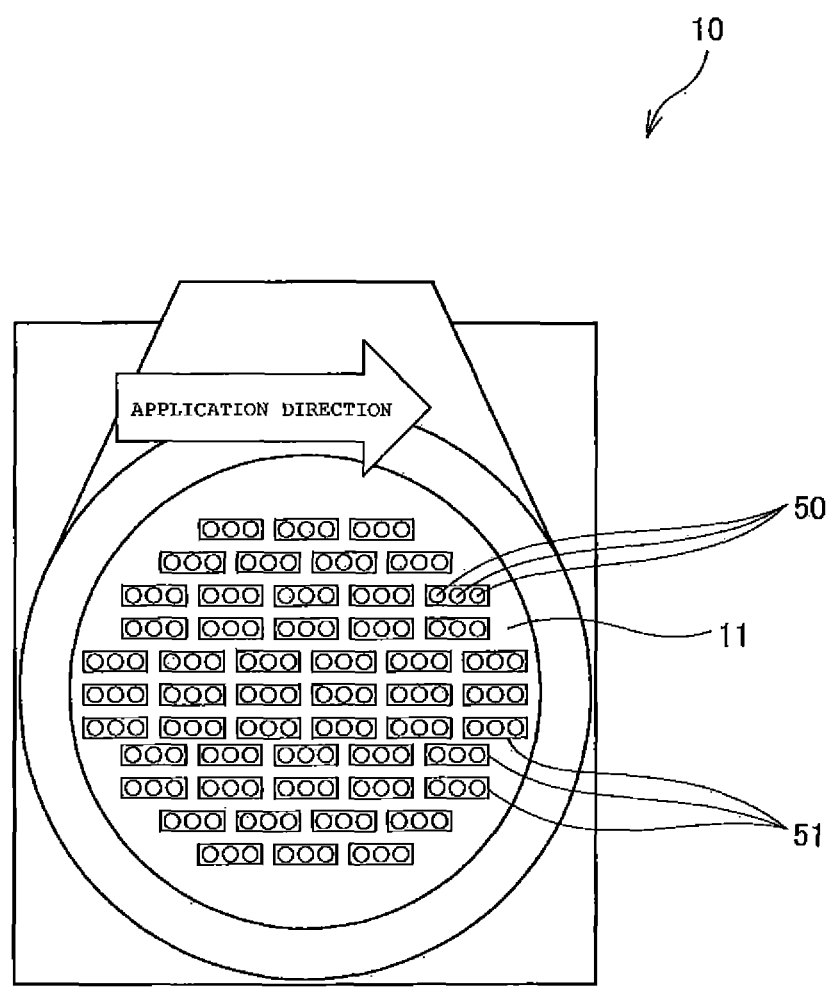
FIG. 6 is a top view to illustrate an arrangement state of antigen (allergen) in a reaction area of the reaction plate.
Figure 7:
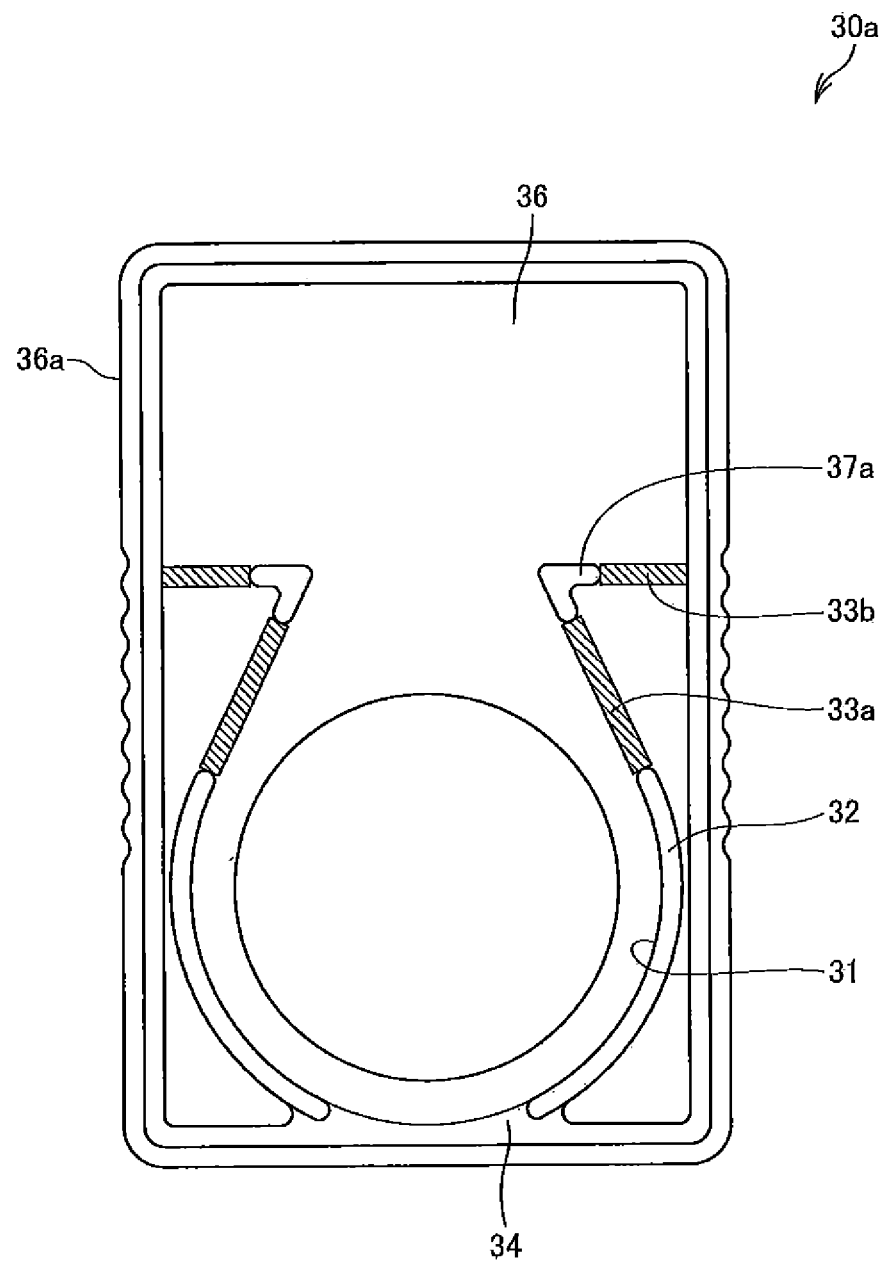
FIG. 7 is a bottom view to illustrate a variant of the cover to be used for the biochemical reaction substrate according to an embodiment of the present invention.
Figure 8:
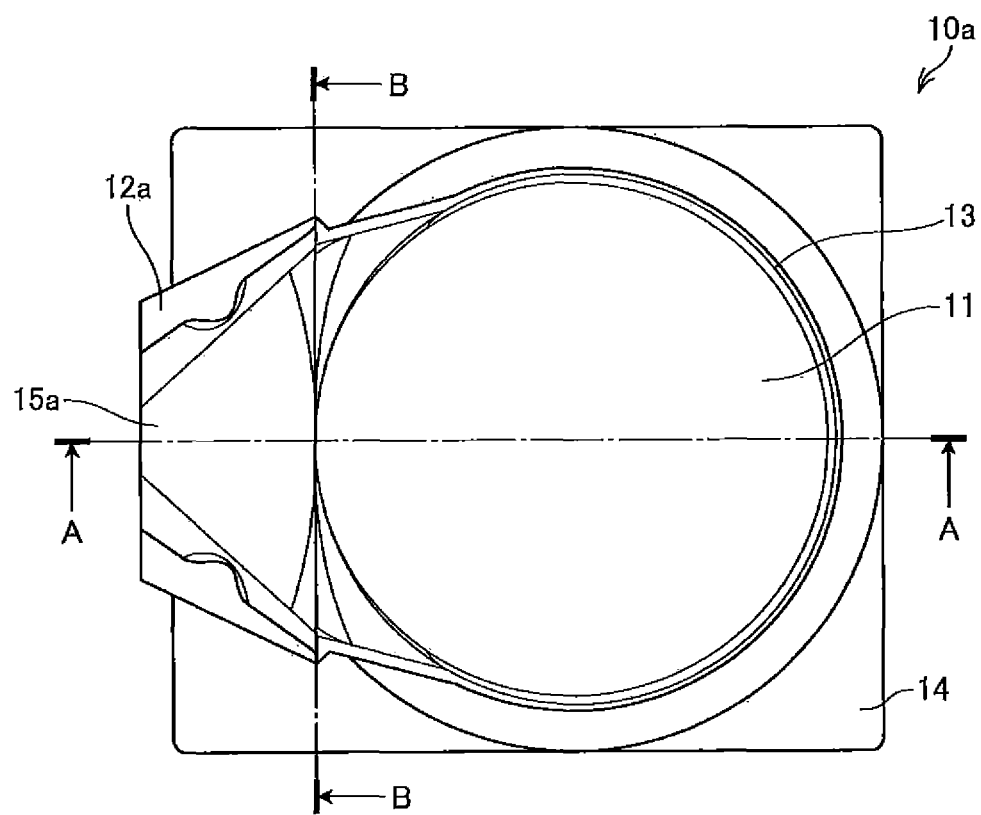
FIG. 8 is a top view to illustrate a variant of the reaction plate to be used for the biochemical reaction substrate according to an embodiment of the present invention.
Figure 9:
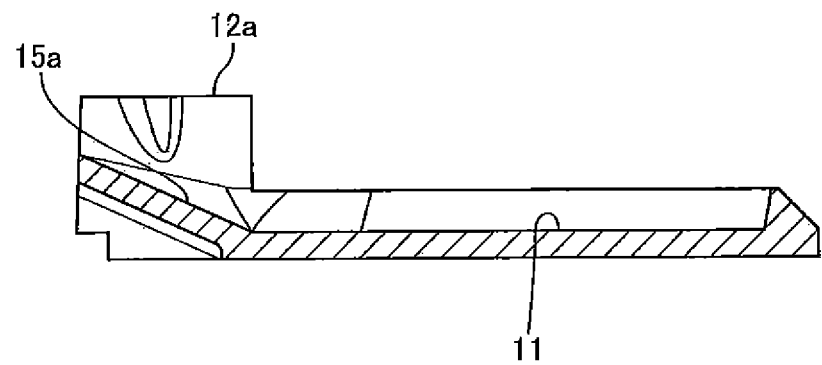
FIG. 9 is an A-A cross-sectional view in FIG. 8.
Figure 10:
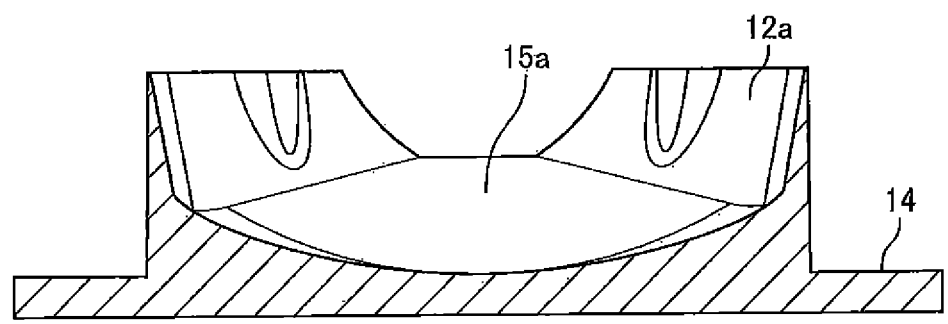
FIG. 10 is a B-B cross-sectional view in FIG. 8.
Figure 11:
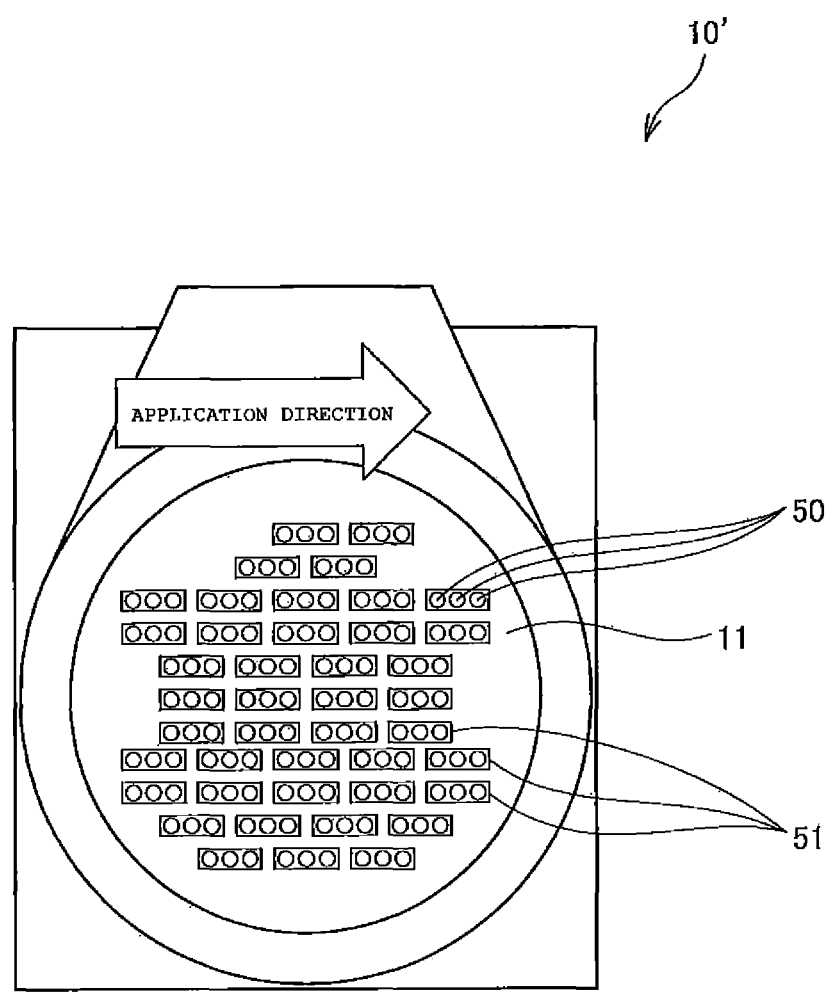
FIG. 11 is a top view to illustrate another arrangement state of antigen (allergen) in a reaction area of the reaction plate.
Figure 12:
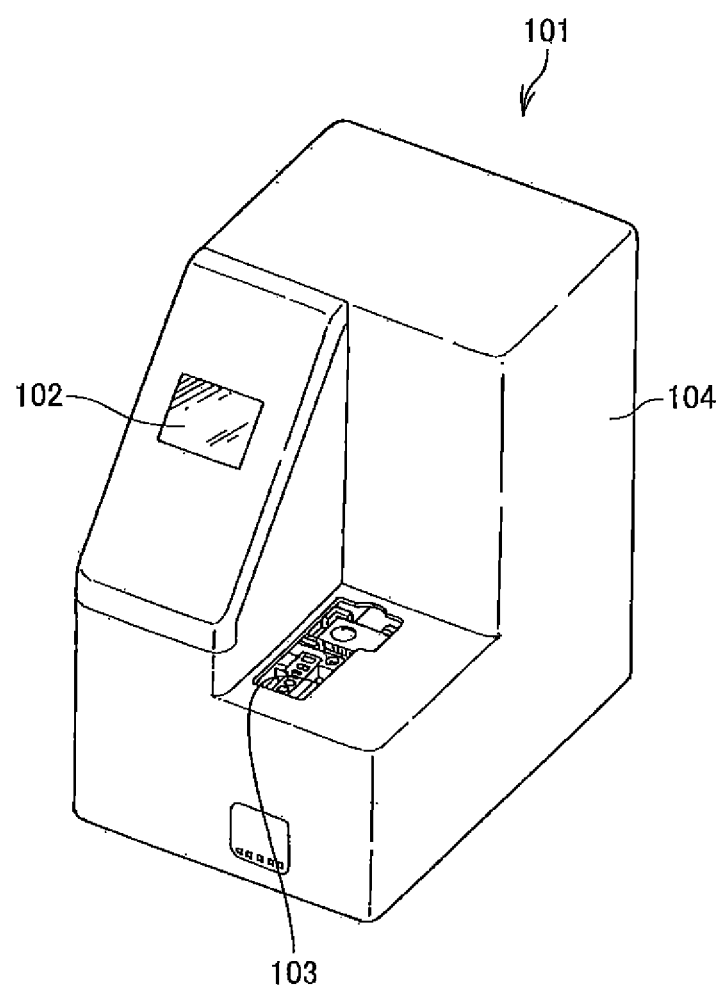
FIG. 12 is a perspective view of an analyzer according to an embodiment of the present invention.
Figure 13:
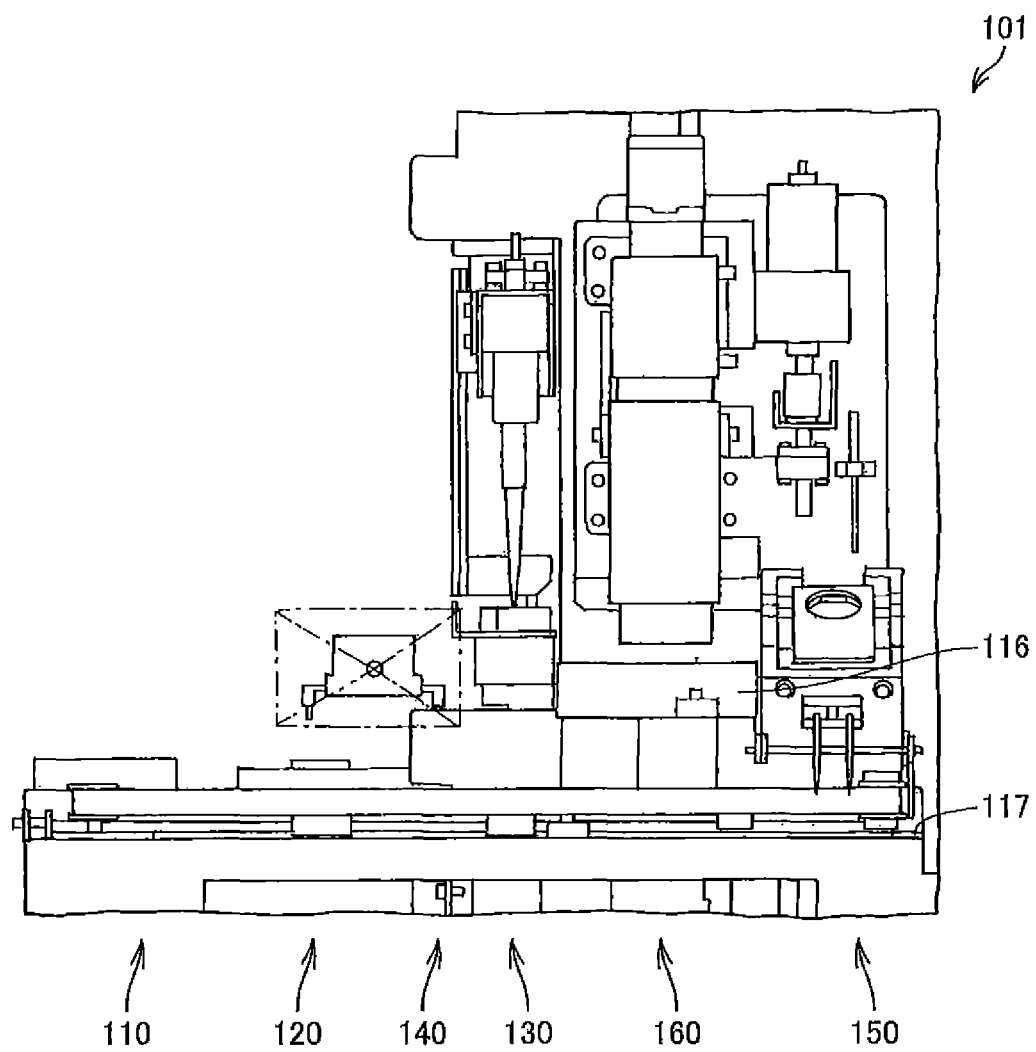
FIG. 13 is a diagram to illustrate an internal structure of the analyzer according to an embodiment of the present invention.
Figure 14:
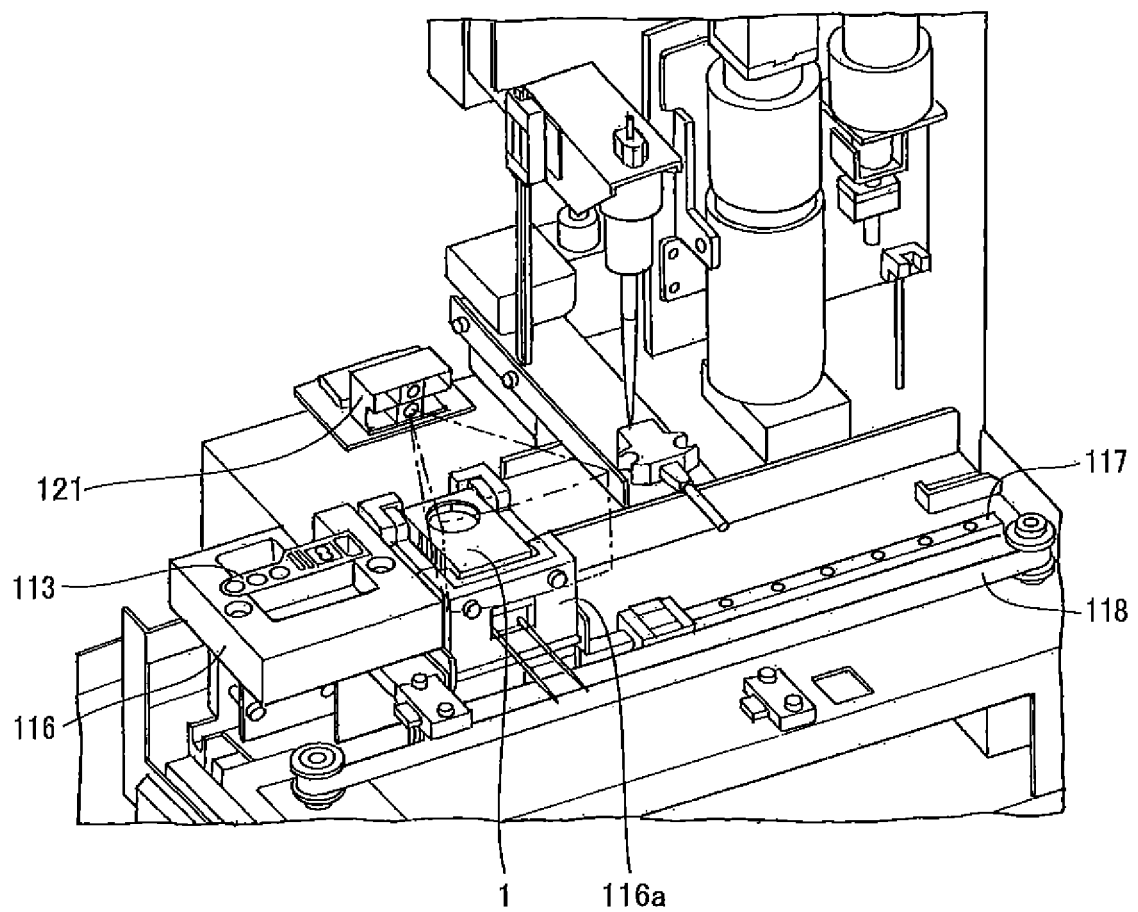
FIG. 14 is a perspective view to illustrate an internal structure of the analyzer according to an embodiment of the present invention.
Figure 15:
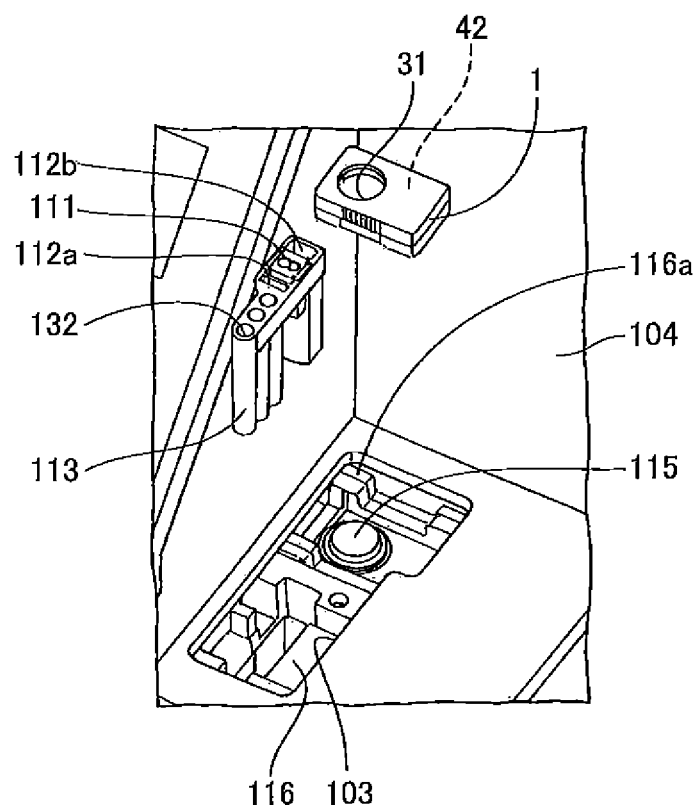
FIG. 15 is a perspective view to illustrate an installation area of the analyzer according to an embodiment of the present invention.
Figure 16:
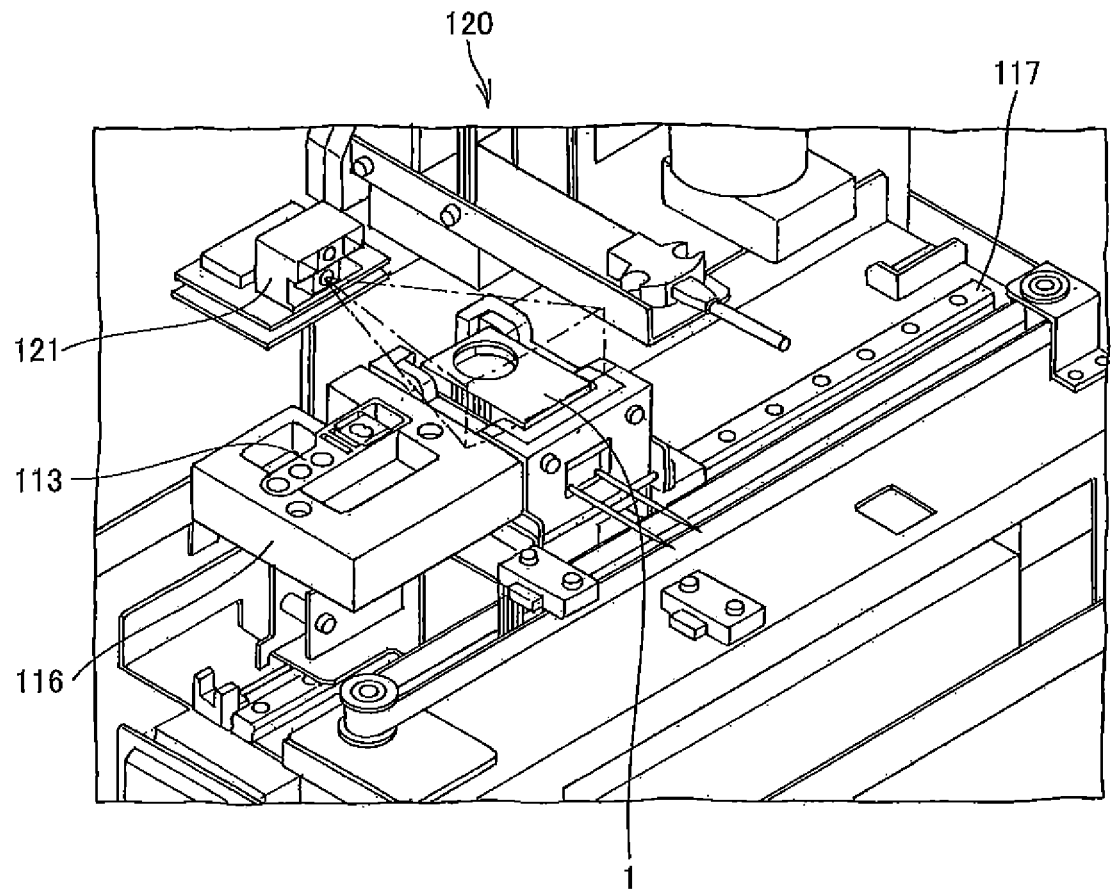
FIG. 16 is a perspective view to illustrate a barcode reading area of the analyzer according to an embodiment of the present invention.
Figure 17:
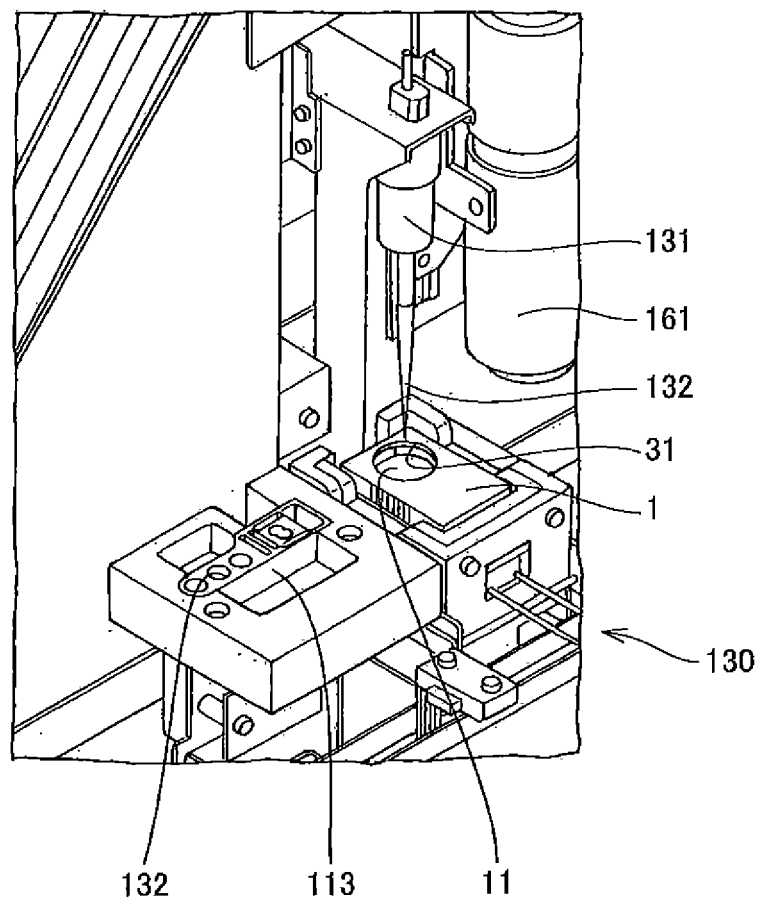
FIG. 17 is a perspective view to illustrate a dispensing area of the analyzer according to an embodiment of the present invention.
Figure 18:
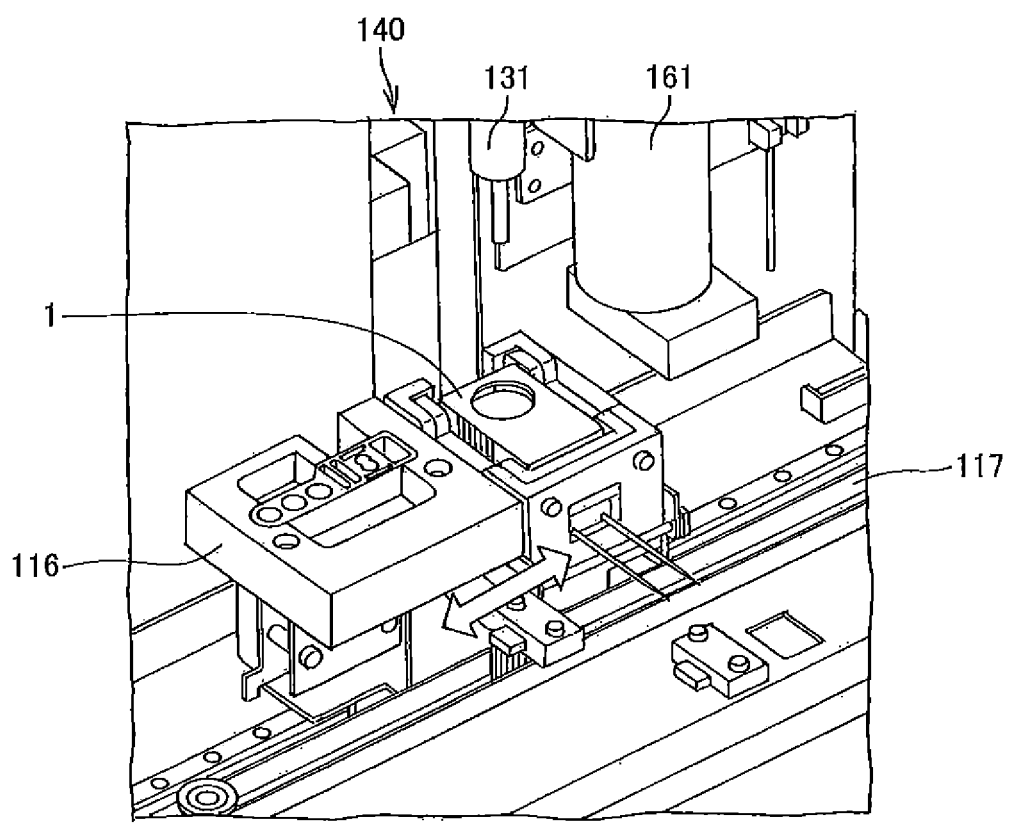
FIG. 18 is a perspective view to illustrate a stirring area of the analyzer according to an embodiment of the present invention.
Figure 19:
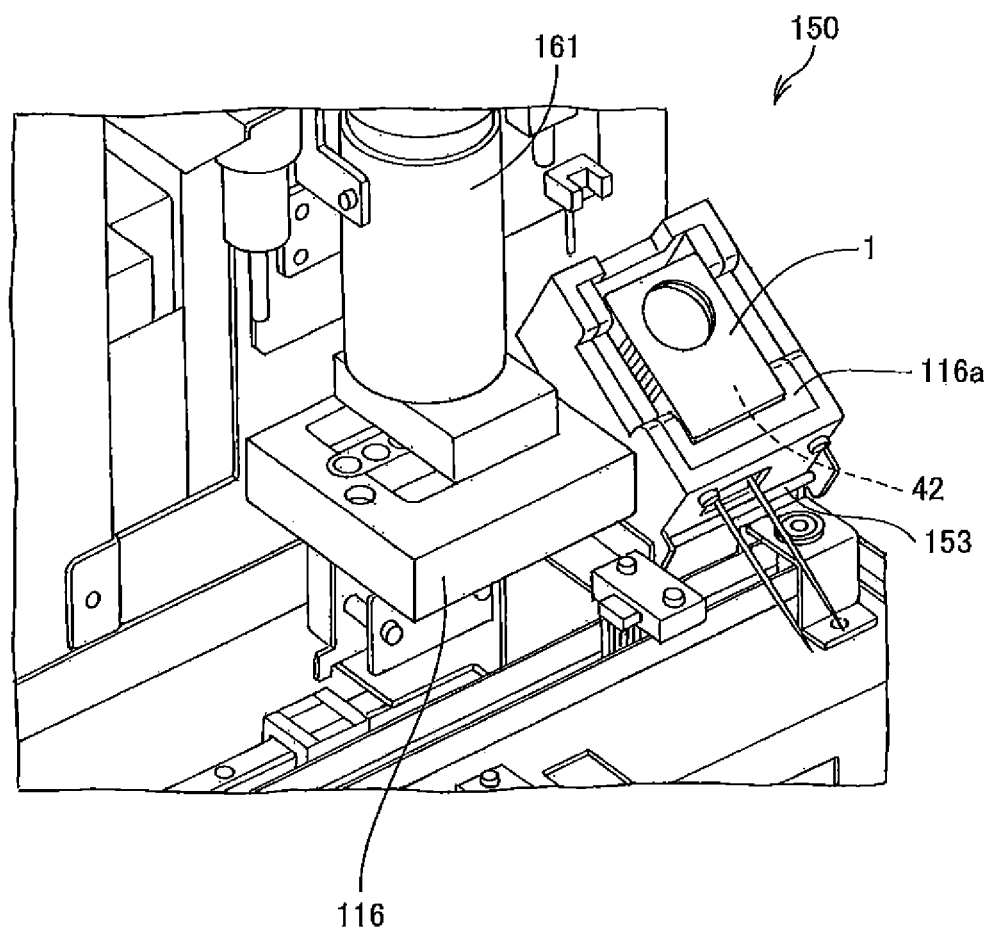
FIG. 19 is a perspective view to illustrate a drainage area of the analyzer according to an embodiment of the present invention.
Figure 20:
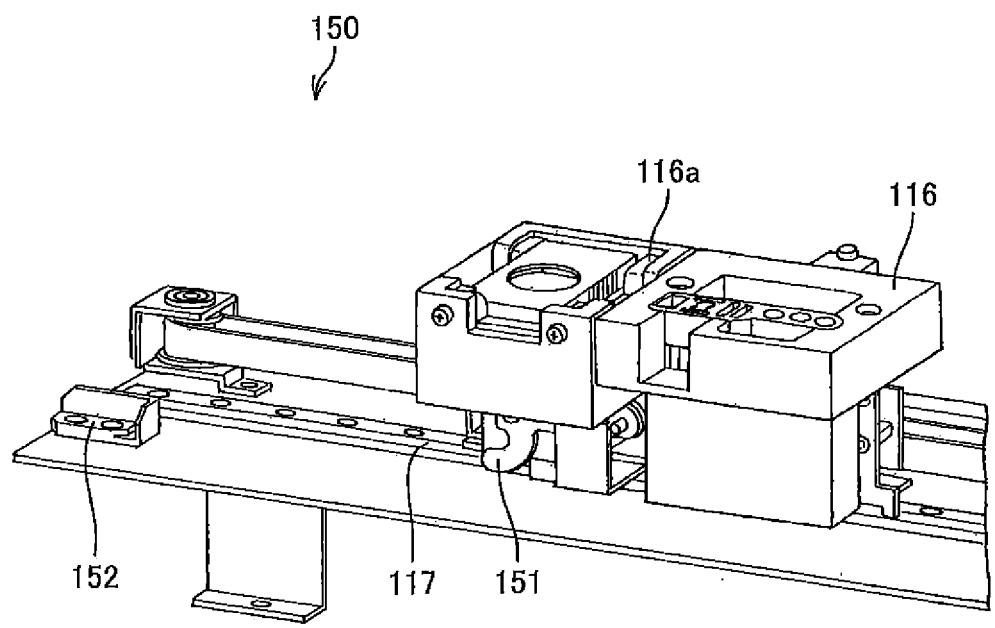
FIG. 20 is a perspective view to illustrate a tilting mechanism of the analyzer according to an embodiment of the present invention.
Figure 21:
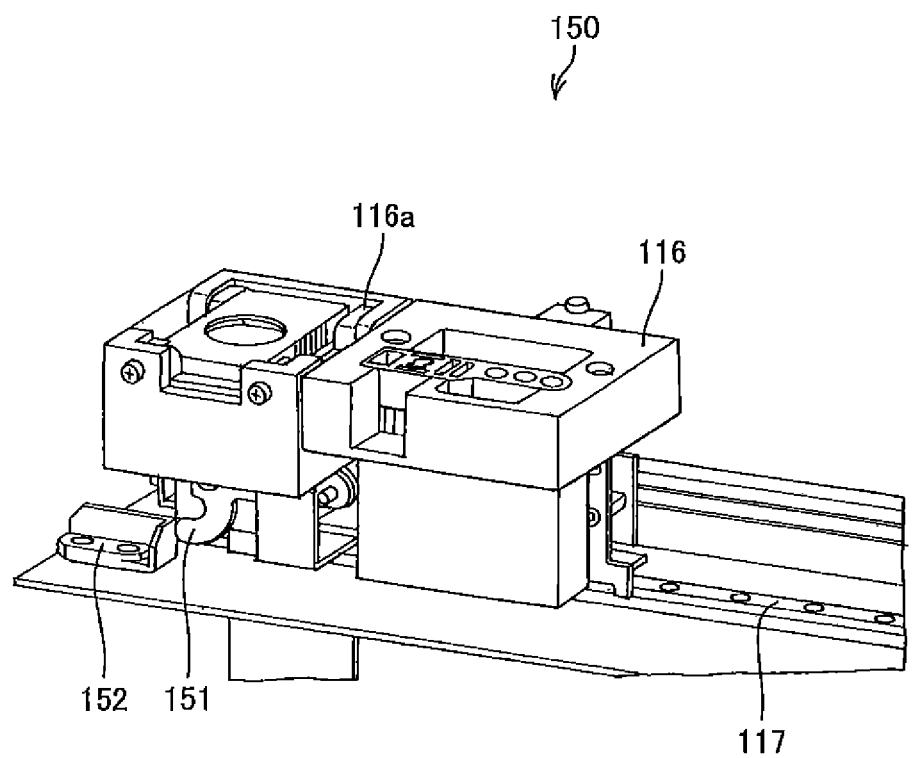
FIG. 21 is a perspective view to illustrate a tilting mechanism of the analyzer according to an embodiment of the present invention, showing a state in which a tilting cam is in abutment with a stopper.
Figure 22:
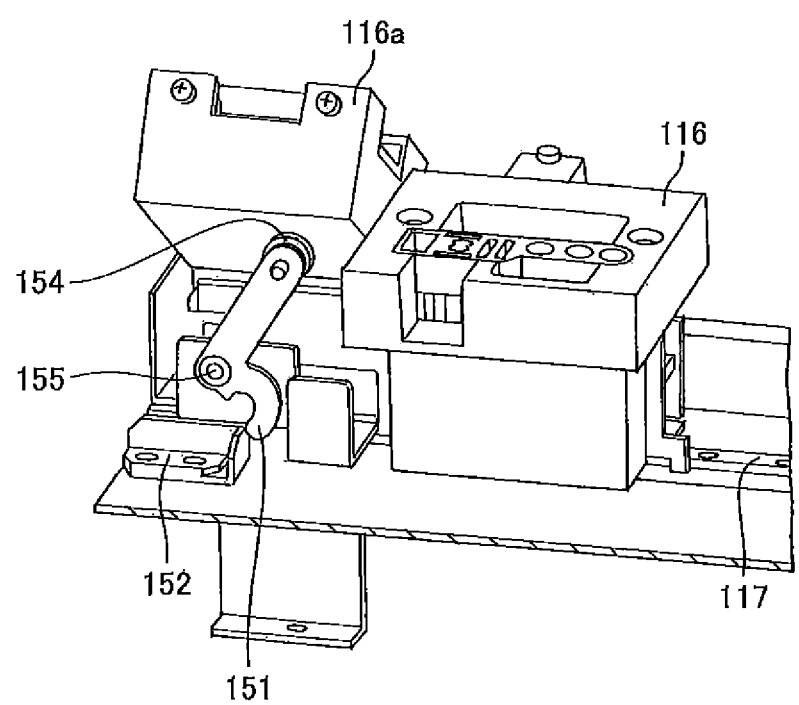
FIG. 22 is a perspective view to illustrate a tilting mechanism of the analyzer according to an embodiment of the present invention, showing a state in which a substrate holding portion is tilted.
Figure 23:
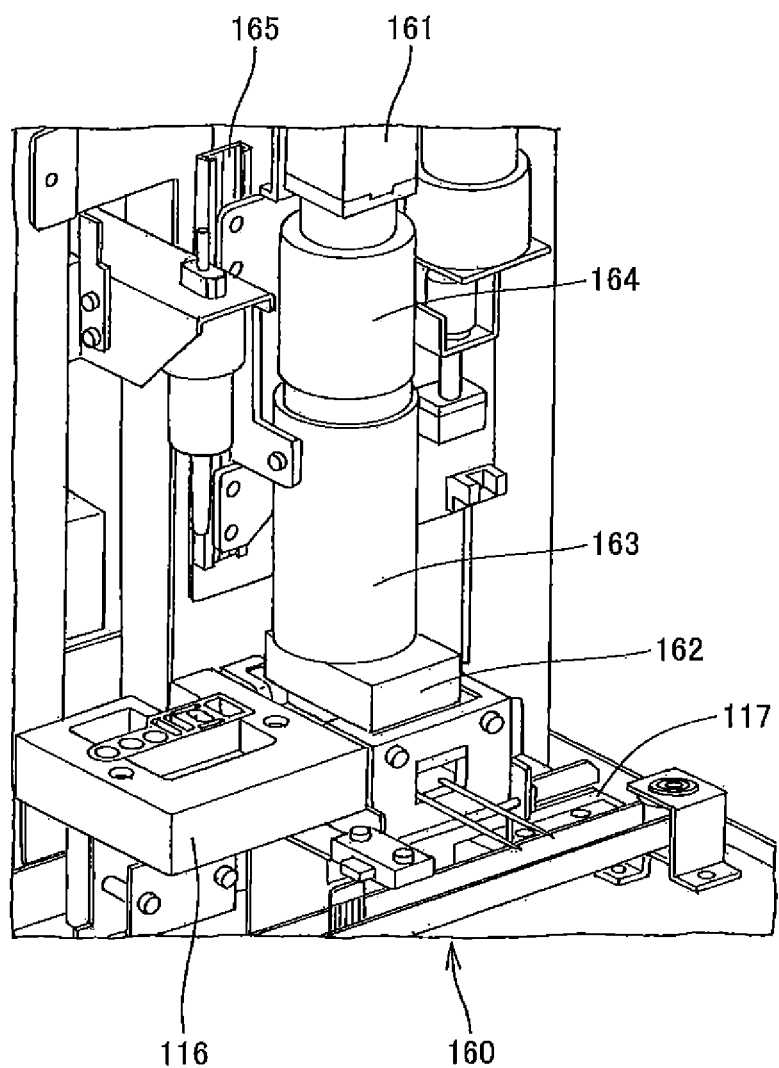
FIG. 23 is a perspective view to illustrate a detection area of the analyzer according to an embodiment of the present invention.
Figure 24:
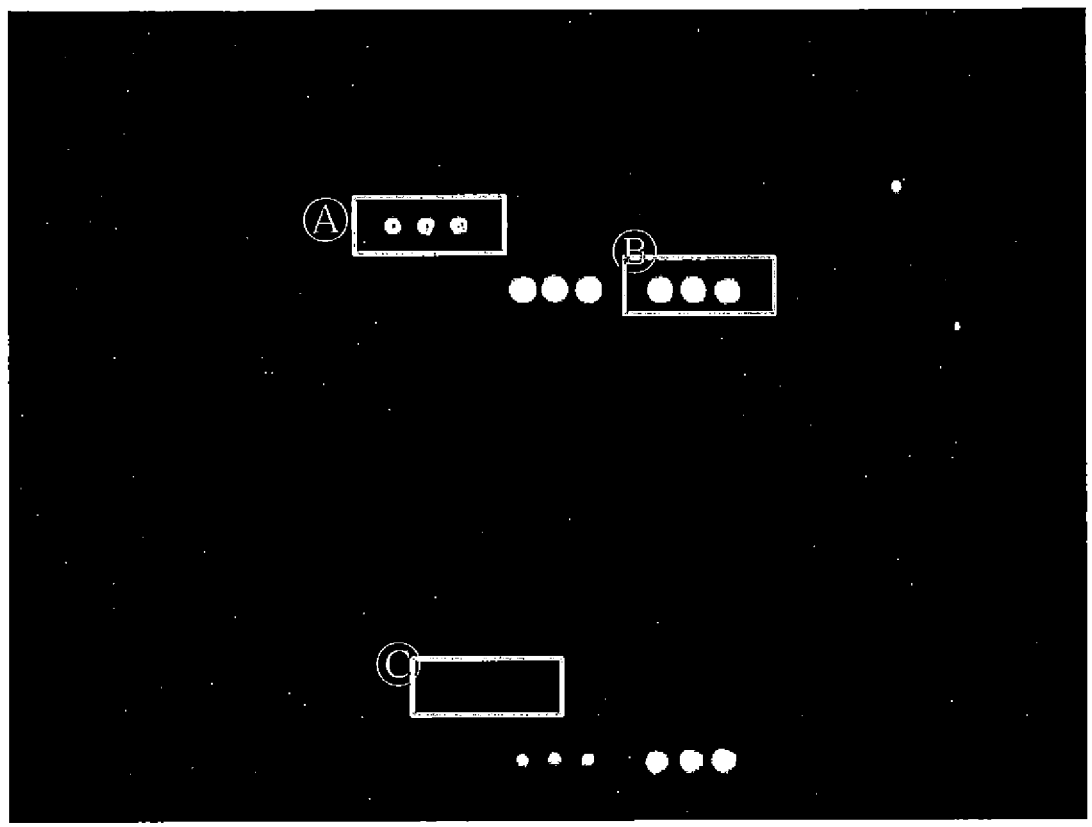
FIG. 24 is a diagram to illustrate detection results of the analyzer according to an embodiment of the present invention, illustrating the arrangement of antigens in the reaction area.
Figure 25:
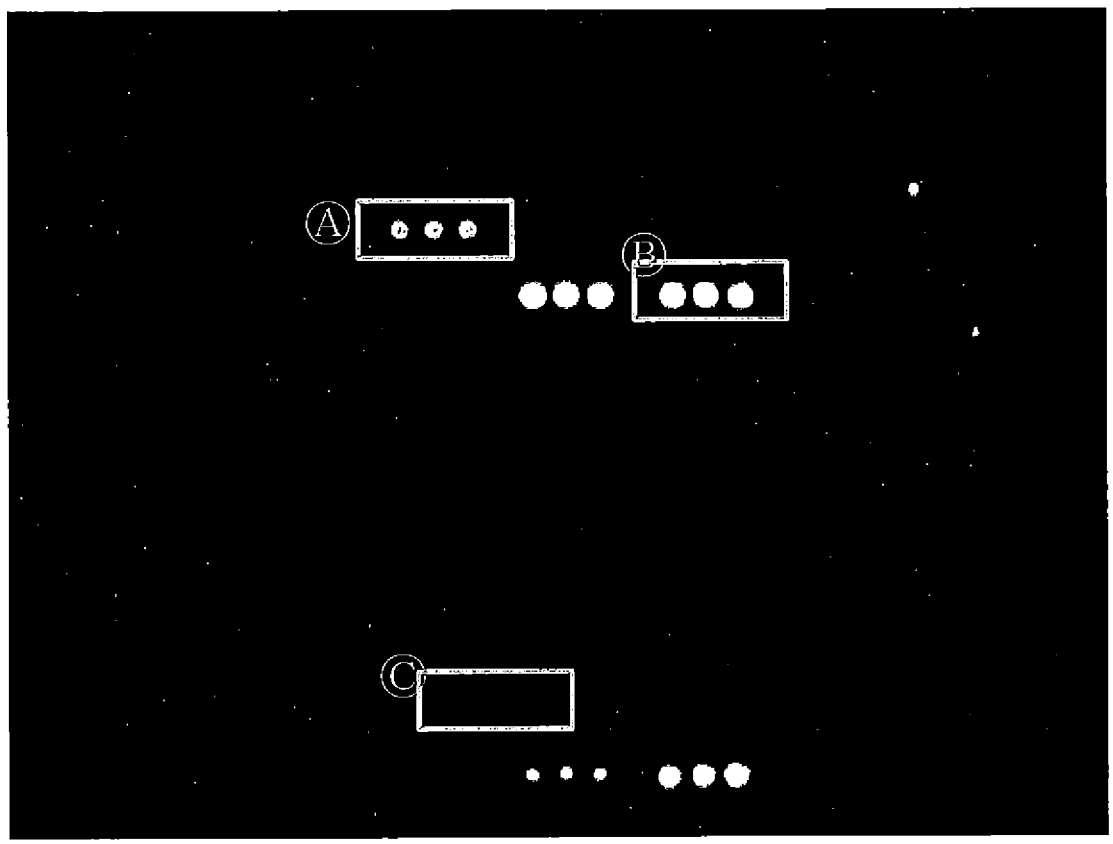
FIG. 25 is a diagram to illustrate detection results of the analyzer according to an embodiment of the present invention, showing a state of being exposed for 60 seconds.
Figure 26:
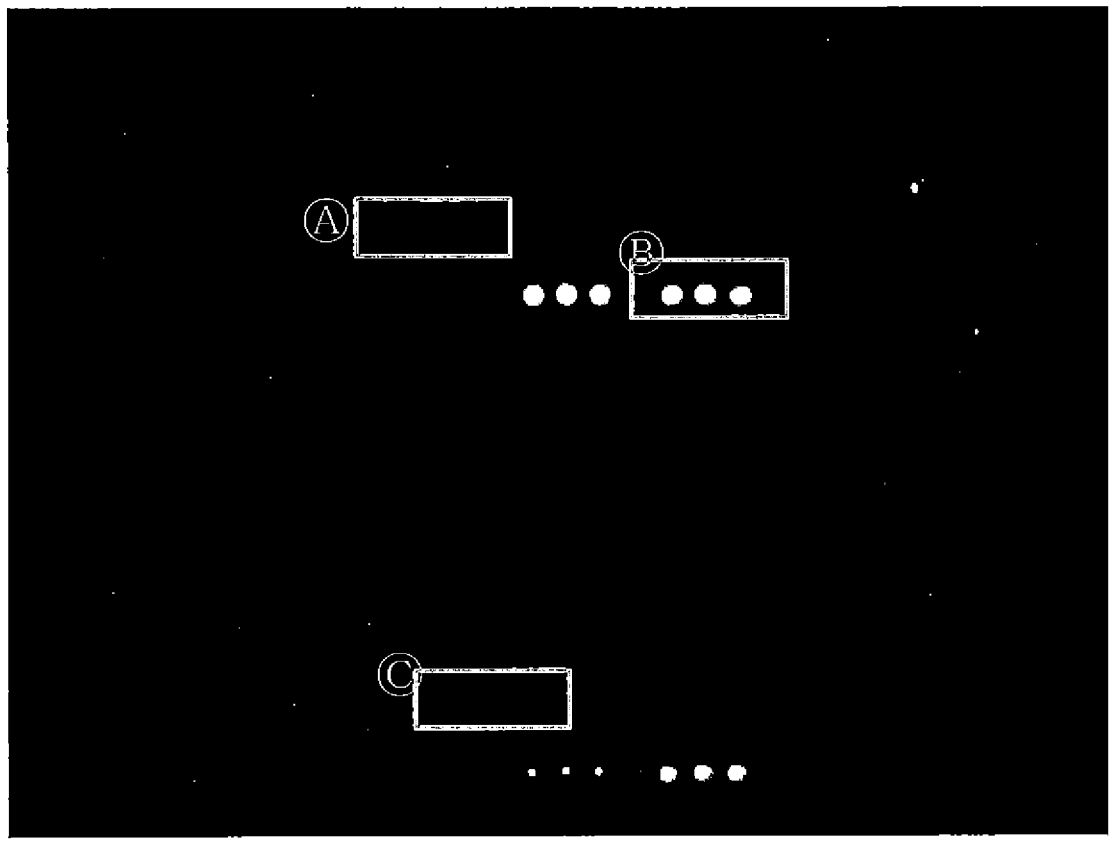
FIG. 26 is a diagram to illustrate detection results of the analyzer according to an embodiment of the present invention, showing a state of being exposed for 20 seconds.
Figure 27:
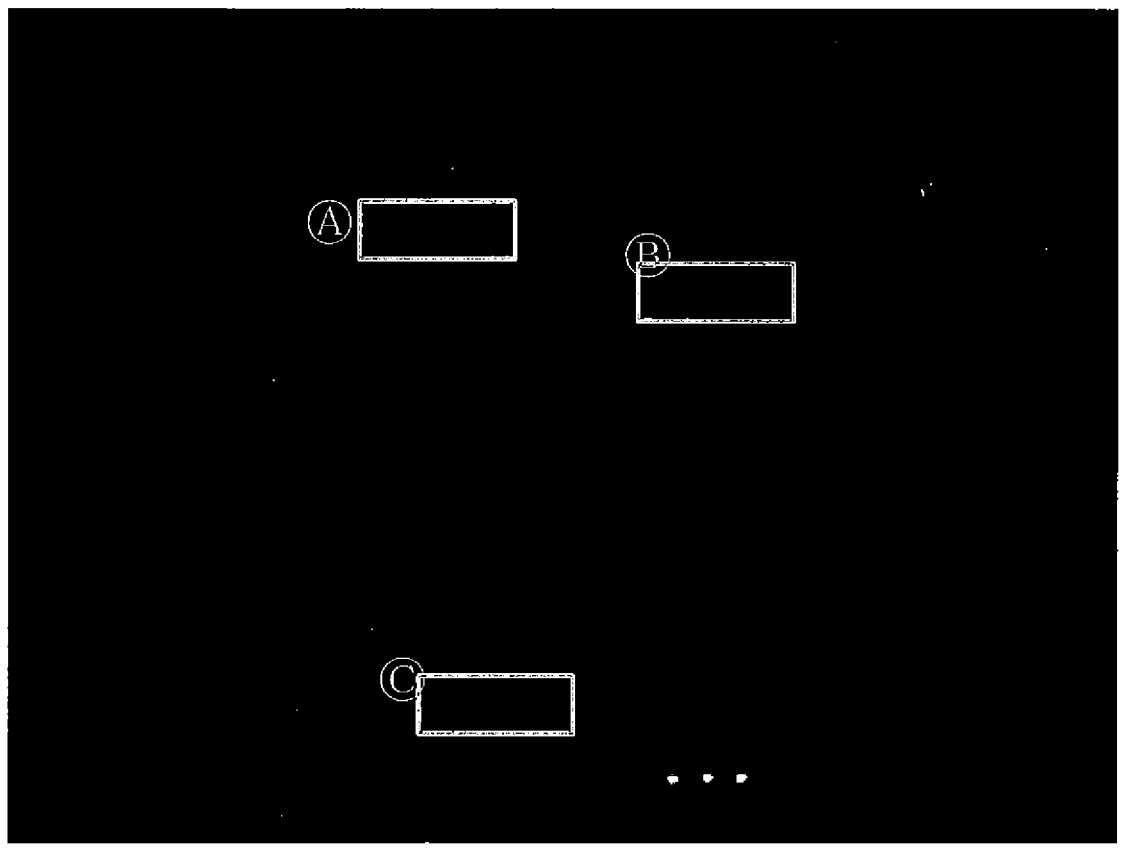
FIG. 27 is a diagram to illustrate detection results of the analyzer according to an embodiment of the present invention, showing a state of being exposed for 5 seconds.

FIG. 1 is a perspective view of a biochemical reaction substrate according to an embodiment of the present invention; FIG. 2 is an exploded view of a biochemical reaction substrate according to an embodiment of the present invention; FIG. 3 is a perspective view of a reaction plate to be used for a biochemical reaction substrate according to an embodiment of the present invention; FIG. 4 is a top view of a storage container to be used for a biochemical reaction substrate according to an embodiment of the present invention; FIG. 5 is a bottom view of a cover to be used for a biochemical reaction substrate according to an embodiment of the present invention; FIG. 6 is a top view to illustrate an arrangement state of antigen (allergen) in a reaction area of the reaction plate; FIG. 7 is a bottom view to illustrate a variant of the cover to be used for the biochemical reaction substrate according to an embodiment of the present invention; FIG. 8 is a top view to illustrate a variant of the reaction plate to be used for the biochemical reaction substrate according to an embodiment of the present invention; FIG. 9 is an A-A cross-sectional view in FIG. 8; FIG. 10 is a B-B cross-sectional view in FIG. 8; FIG. 11 is a top view to illustrate another arrangement state of antigen (allergen) in a reaction area of the reaction plate; FIG. 12 is a perspective view of an analyzer according to an embodiment of the present invention; FIG. 13 is a diagram to illustrate an internal structure of the analyzer according to an embodiment of the present invention; FIG. 14 is a perspective view to illustrate an internal structure of the analyzer according to an embodiment of the present invention; FIG. 15 is a perspective view to illustrate an installation area of the analyzer according to an embodiment of the present invention; FIG. 16 is a perspective view to illustrate a barcode reading area of the analyzer according to an embodiment of the present invention; FIG. 17 is a perspective view to illustrate a dispensing area of the analyzer according to an embodiment of the present invention; FIG. 18 is a perspective view to illustrate a stirring area of the analyzer according to an embodiment of the present invention; FIG. 19 is a perspective view to illustrate a drainage area of the analyzer according to an embodiment of the present invention; FIG. 20 is a perspective view to illustrate a tilting mechanism of the analyzer according to an embodiment of the present invention; FIG. 21 is a perspective view to illustrate a tilting mechanism of the analyzer according to an embodiment of the present invention, showing a state in which a tilting cam is in abutment with a stopper; FIG. 22 is a perspective view to illustrate a tilting mechanism of the analyzer according to an embodiment of the present invention, showing a state in which a substrate holding portion is tilted; FIG. 23 is a perspective view to illustrate a detection area of the analyzer according to an embodiment of the present invention; FIG. 24 is a diagram to illustrate detection results of the analyzer according to an embodiment of the present invention, illustrating the arrangement of antigens in the reaction area; FIG. 25 is a diagram to illustrate detection results of the analyzer according to an embodiment of the present invention, showing a state of being exposed for 60 seconds; FIG. 26 is a diagram to illustrate detection results of the analyzer according to an embodiment of the present invention, showing a state of being exposed for 20 seconds; and FIG. 27 is a diagram to illustrate detection results of the analyzer according to an embodiment of the present invention, showing a state of being exposed for 5 seconds.

As shown in FIGS. 1 and 2, a biochemical reaction substrate 1 according to the present embodiment can store a reaction plate 10 therein, and has a cover 30 and a storage container 40. A substantially circular injection hole 31 is formed in the cover 30, and the injection hole 31 is configured to be disposed at a position corresponding to a reaction area 11 of the reaction plate 10 in a state where the reaction plate 10 is stored. Moreover, a concave heated portion 43 is formed on the bottom of the storage container 40, and is configured such that a heater of a testing device to be described later can abut against and heat the reaction area 11.

As shown in FIG. 2, an absorber storing portion 42 which stores a reaction plate storing portion 41 for storing the reaction plate 10, and an absorber storing portion 42 for storing an absorber 20 made of a porous material such as sponge capable of absorbing a sufficient amount of liquid is formed in the storage container 40. Note that in a state where the reaction plate 10 and the absorber 20 are stored in the storage container 40, the distal end of the flow passage 12 formed in the reaction plate 10 is disposed so as to abut against the absorber 20.

As shown in FIG. 3, the reaction plate 10 includes: a planar base portion 14 that can be fitted into the reaction plate storing portion 41 formed in the storage container 40 without any difficulty; a flow-out prevention wall 13 standing upright from the base portion 14; and a flow passage 12. The flow-out prevention wall 13 is a substantially annular wall, and the inside of the flow-out prevention wall 13 is defined as a reaction area 11.

Moreover, at a position facing the absorber 20 from the reaction area 11, a flow passage 12 is formed so as to extend from the outer peripheral edge of the flow-out prevention wall 13 and such that the distance between a pair of side walls is gradually decreased. The flow passage 12 is formed to drain the specimen or the like dispensed to the reaction area 11 and cause the absorber 20 to absorb it, and the flow passage 12 has a slope 15 formed in such a way to climb up from the reaction area 11 such that the specimen or the like can be discharged from the reaction area 11 toward the absorber 20 without waste by tilting the biochemical reaction substrate 1. The slope 15 is preferably formed to be inclined from the base portion 14 by about 5° to 70°, a more preferable angle of inclination is 12° to 50°, a further preferable angle is 17° to 35°, and a suitable angle is 23°. The larger the angle of inclination of the flow passage, the more the leakage can be prevented, but a situation in which discharging is difficult becomes likely to occur. Therefore, by adopting a preferable angle, it is possible to achieve the object of the present invention. The proximal end of the flow passage 12 on the reaction area 11 side is configured to be as wide as possible to smoothly guide the specimen or the like on the reaction area 11 to the distal end on the absorber 20 side, and the distal end side of the flow passage 12 is formed such that the slope 15 abuts against the absorber 20 at an acute angle.

As described above, in the reaction plate 10 used in the biochemical reaction substrate 1 according to the present embodiment, since the flow-out prevention wall 13 is formed so as to surround the reaction area 11, and the slope 15 is provided in the flow passage 12, it becomes possible, in the allergy test, to prevent the specimen or the like from flowing out from the reaction area 11 even when the biochemical reaction substrate 1 is stirred, and to easily discharge the specimen or the like from the flow passage 12 when the specimen or the like is drained after stirring. In addition, non-specific adsorption can be suppressed by applying a blocking agent to the entire reaction area in advance. Further, by defining the inside of the flow-out prevention wall 13 as the reaction area, it is possible to more easily discharge the specimen or the like as a side effect of applying the blocking agent.

Further, as the blocking agent, a synthetic polymer not originating from animals and plants, such as polyethylene glycol, can be used in general technique, and it can be appropriately selected and used according to the properties of the material of the reaction plate 10, a target substance such as an antigen, a specimen such as blood, and a reagent such as a cleaning solution.

As shown in FIG. 4, the storage container 40 may have a reaction plate storing portion 41 and an absorber storing portion 42 formed therein. Further, the storage container 40 is a bottomed box-shaped member having an open end on the upper side, and when a rib 45 is formed on the inner wall of the absorber storing portion 42, it becomes possible to hold the absorber 20 more reliably. Further, it is preferable that the reaction plate storing portion 41 has an opening portion 46 formed at a position corresponding to the reaction area 11 when the reaction plate 10 is placed thereon. Further, the storage container 40 can directly heat the reaction area 11 from outside of the biochemical reaction substrate 1 through the opening portion 46.

Further, the reaction plate storing portion 41 and the absorber storing portion 42 are made in communication with each other through the storage portion groove 44, and even if the specimen or the like leaks out of the flow-out prevention wall 13 due to stirring or the like, configured is made such that the specimen or the like can be guided from the reaction plate storing portion 41 to the absorber storing portion 42.

As shown in FIG. 5, the cover 30, which is a member that closes the open end of the storage container 40 described above and constitutes an outer shell of the biochemical reaction substrate 1, has a side wall portion 36a that hangs down and extends from the outer peripheral edge of the top side 36. Further, an inner wall portion 32 is formed so at to hang down to the top side 36 at a position corresponding to the flow-out prevention wall 13 of the reaction plate 10, and when the reaction plate 10 is stored in the biochemical reaction substrate 1, the inner wall portion 32 is in abutment with the flow-out prevention wall 13.

Further, a defining wall 37 extending downward from the top side 36 is formed at a position corresponding to a continuous portion between the reaction plate storing portion 41 of the storage container 40 and the absorber storing portion 42. The defining wall 37 separates the reaction area 11 of the reaction plate 10 from the absorber 20. Note that the inner wall portion 32 and the defining wall 37 are formed discontinuously with each other via a missing portion 33. If the inner wall portion 32 is extended to a part of the missing portion 33, a minute gap is generated between the outer periphery of the flow passage 12 and the inner wall portion 32, and there is a risk of leakage to the outside seen from the reaction area of the flow-out prevention wall 13 by a capillary phenomenon due to the presence of the gap, or there is a risk that the specimen or the like absorbed by the absorber 20 may flow back to the reaction area 11 side; therefore, the missing portion 33 is provided to prevent this.

Further, the inner wall portion 32 may have a missing portion for adjustment 34 formed at an end portion in the longitudinal direction of the cover 30. Forming a part of the inner wall portion 32 as an inner wall of the side wall portion 36a enables space saving and cost reduction of material cost and the like.

In addition, the side wall portion of the outer periphery of the cover 30 is configured to have a rugged-shaped slip prevention device 35 so that the examiner can surely grasp the biochemical reaction substrate 1 by the slip prevention device 35. Further, a rib 38 may be formed on the inner wall of the side wall portion 36a corresponding to the absorber storing portion 42 as in the absorber storing portion 42.

Note that as shown in FIG. 6, a plurality of sets (for example, 3 spots/one set) of antigens 50 are arranged in a predetermined number of sets (for example, 156 spots/52 sets) in the reaction area 11 of the reaction plate 10. Arranging in this way makes it possible to increase the amount of the antigen 50 placed on the reaction area 11, and to detect a plurality of allergic reactions by one test. This can be achieved by making the type of the antigen the same for each set, and setting a distance between the sets to eliminate the influence during measurement. The distance between the sets is preferably 0.5 mm or more, more preferably 0.5 mm to 2.0 mm, further preferably 0.8 mm to 1.6 mm, and suitably about 1.2 mm. This makes it possible to perform, for example, the test of IgE antibody in a blood sample against different types of antigens (allergens) all at once. Therefore, this test can reduce the amount of specimen, and reduce the time and the number of steps.

Note that as shown in FIG. 7, the defining wall portion 37a, the inner wall portion 32 and the side wall portion 36a may be formed discontinuously, by forming a defining wall portion 37a in a substantially L shape such that the inner wall portion 32 and the defining wall 37 are continuous like the shape of the missing portion of the cover 30a, and forming the inner wall missing portion 33a in the inner wall portion 32 and the defining wall missing portion 33b in the defining wall, respectively. Since there is a risk that leakage occurs to the outside as seen from the reaction area of the flow-out prevention wall 13 due to the capillary phenomenon, or the specimen or the like absorbed by the absorber 20 flows back to the reaction area 11 side, this is prevented by forming the inner wall missing portion 33a and the defining wall missing portion 33b in this manner.

Further, as shown in FIGS. 8 to 10, it is preferable to form a slope 15a formed in the flow passage portion 12a of the reaction plate 10a such that the specimen or the like can be discharged more easily. As shown in FIG. 9, the slope 15a is smoothly formed in a continuous portion with the reaction area 11 such that the specimen or the like can be discharged without waste, thus preventing the specimen or the like from staying in the continuous portion between the reaction area 11 and the slope 15a. Further, as shown in FIG. 10, the cross-sectional shape of the slope 15a itself is also configured to have a smooth curve, thereby preventing the specimen and the like from staying on the slope 15a.

Further, it is preferable that the antigens 50 arranged in the reaction area 11 are arranged such that they are concentrated in the middle of the reaction plate 10 as shown in FIG. 11. By adjusting the arrangement position of the antigens 50 in this way, it is possible to reduce the time for converting the antigens 50 into a solid phase on the reaction plate 10.

Next, with reference to FIGS. 12 to 23, the operation of an analyzer for performing an allergy test using the biochemical reaction substrate 1 according to the present embodiment will be described.

As shown in FIG. 12, an analyzer 101 according to the present embodiment includes a housing 104 having an operating panel 102, and a loading section 103 for installing a reagent cartridge 113 to be described later and the biochemical reaction substrate 1. The loading section 103 can be opened and closed by an installation door (not shown).

As shown in FIG. 13, the inside of the analyzer 101 is defined into the installation area 110, a barcode reading area 120, a dispensing area 130, a stirring area 140, a detection area 160, and a drainage area 150 which are arranged on the same straight line. Further, a moving table 116 guided by a guide device 117 arranged on the same straight line is movably mounted in a range from the installation area 110 to the drainage area 150. Further, adjacent areas may be configured to overlap with each other in such a way as that in the stirring area 140 and the dispensing area 130, an overlapping portion may occur in these areas.

As shown in FIG. 14, the moving table 116 includes a substrate holding portion 116a on which the reagent cartridge 113 is placed and also the biochemical reaction substrate 1 is placed. Further, a driving section 118 extending substantially in parallel with the guide device 117 is attached thereto, and the driving section 118 is wound around with a ring-shaped band, which is rotated by a drive source such as a motor (not shown), and is configured to be able to move the moving table 116 along the guide device 117 by transmitting the driving force of the band to the moving table 116.

Next, each area of the installation area 110, the barcode reading area 120, the dispensing area 130, the stirring area 140, the detection area 160, and the drainage area 150 will be described.

As shown in FIGS. 13 and 15, the installation area 110 is located at one end side (left end in FIG. 13) of the guide device 117. Further, as shown in FIG. 15, configuration is made such that when the moving table 116 is located in the installation area 110, the reagent cartridge 113 and the biochemical reaction substrate 1 can be installed from the outside of the housing 104 to the moving table 116 via the loading section 103. The reagent cartridge 113 is configured to be able to store a specimen 111, a reaction reagent 112a, a cleaning solution 112b, and a chip 132. Note that in the description of the present application, the reaction reagent 112a and the cleaning solution 112b are collectively referred to as a "reagent 112" hereinafter. The biochemical reaction substrate 1 includes an injection hole 31 opening toward the reaction area 11 for dispensing the specimen 111 and the reagent 112 as described above, and the absorber storing portion 42 for draining the excessive specimen 111 and reagent 112 after stirring the biochemical reaction substrate 1 after dispensing the specimen 111 and the reagent 112. An absorber not shown is stored in the absorber storing portion 42, and excessive specimen 111 and reagent 112 are held by the absorber so as not to flow to the outside. Note that the reaction reagent is a reagent for a reaction necessary for detection, and refers to, for example, a labeled antibody and a luminescent substrate. The reaction reagent may be any reagent necessary for the reaction and is not particularly limited to these specific examples. Moreover, the positions for disposing the reaction reagent 112a and the cleaning solution 112b may be appropriately determined, and are not limited to the positions shown in FIG. 15.

Further, a heating section 115 is attached to the substrate holding portion 116a, on which the biochemical reaction substrate 1 is installed, so as to correspond to the reaction area 11 of the biochemical reaction substrate 1 so that attempt is made to reduce the reaction time by heating the reaction area to a body temperature (for example, about 37° C.) with the heating section 115.

Next, as shown in FIG. 16, the moving table 116 is moved to the barcode reading area 120 along the guide device 117. A barcode reader 121 is attached to the barcode reading area 120 so that the analyzer 101 reads reagent information such as a reagent, reagent expiration date and lot, calibration curve knowledge information, etc. by reading the barcodes respectively printed or affixed on the side walls of the reagent cartridge 113 and the biochemical reaction substrate 1 with the barcode reader 121.

As shown in FIG. 17, the dispensing area 130 includes a dispensing nozzle 131 that is attached so as to be movable in a direction substantially perpendicular to the guide device 117. The dispensing nozzle 131 is a member that sucks and ejects the specimen 111 and the reagent 112 stored in the reagent cartridge 113 and dispenses the specimen 111 and the reagent 112 to the biochemical reaction substrate 1. In this dispensing, first, in order to fit a chip 132 stored in the reagent cartridge 113 to the distal end of the dispensing nozzle 131, the moving table 116 is moved such that the position of the chip 132 stored in the reagent cartridge 113 is located directly below the dispensing nozzle 131, and thereafter, the dispensing nozzle 131 is lowered to fit the chip 132 to the distal end of the dispensing nozzle 131.

Next, in order to suck the specimen 111 and the reagent 112 or the like of the moving table 116 from the reagent cartridge 113, the moving table 116 is moved such that the position where the specimen 111 or the reagent 112 or the like of the moving table 116 is located directly below the dispensing nozzle 131, and the specimen 111 or the reagent 112 is sucked respectively. Similarly, after the specimen 111 or the reagent 112 is sucked, the moving table 116 is moved such that the injection hole 31 of the biochemical reaction substrate 1 is located directly below the dispensing nozzle 131, and the sucked specimen 111 and reagent 112 or the like is dispensed into the reaction area 11 through the injection hole 31 of the biochemical reaction substrate 1.

The used chip 132 is separated from the dispensing nozzle 131 and returned to a predetermined position of the reagent cartridge 113. At this time, since it is made unnecessary to provide a position for collecting the used chip 132 by returning the used chip 132 to the original position, the size of the reagent cartridge 113 can be reduced and the used chip 132 can be reliably collected.

The stirring area 140 is located between the dispensing area 130 and the barcode reading area 120. As shown in FIG. 18, the moving table 116 is moved reciprocally in the stirring area 140 along the guide device 117 to appropriately stir the dispensed specimen 111 and reagent 112. At this time, the dispensing nozzle 131 and a detection camera 161 to be described later are configured to retract upward so as not to interfere with the moving table 116 during stirring. Further, while the stirring may be performed at any speed as long as the specimen 111 and the reagent 112 can be stirred reliably, for example, the stirring is preferably performed at a speed at which the moving table 116 can be moved about 60 to 160 times per minute with an amplitude of 1 cm; more preferably, the moving table is stirred at a stirring speed of about 100 to 160 times a minute; furthermore preferably, the moving table is stirred at a stirring speed of about 120 to 160 times a minute; and optimally, the moving table is stirred at a stirring speed of about 140 times a minute.

Next, as shown in FIG. 19, the moving table 116 is moved to the drainage area 150, and drainage is performed by causing excessive specimen 111 and reagent 112 to be absorbed by the absorber 20 stored in the absorber storing portion 42 of the biochemical reaction substrate 1. The drainage area 150 is disposed at the other end portion of the guide device 117, and a stopper 152 is attached to the end portion of the guide device 117 as shown in FIG. 20. In addition, the moving table 116 includes a tilting mechanism by which the substrate holding portion 116a is tilted at a predetermined angle when the moving table 116 reaches the drainage area 150. Such tilting of the substrate holding portion 116a by this tilting mechanism allows the specimen 111 and the reagent 112 to be smoothly drained from the reaction area 11 of the biochemical reaction substrate 1 to the absorber storing portion 42. Note that while the tilting angle by the tilting mechanism may be formed to any extent as long as smooth drainage can be performed and, for example, the tilting angle may be usable in a range of 90° from the same angle as that of the slope 15 formed between the reaction area 11 in the biochemical reaction substrate 1 and the absorber storing portion 42, the tilting mechanism is preferably configured to be tilted at 23° or more; more preferably configured to be tilted at 30° to 70°; further preferably, configured to be tilted at 30° to 60°; and optimally, configured to be tilted at 50°.

Next, the operation of the tilting mechanism will be described with reference to FIGS. 19 to 22. A tilting cam 151 is attached to the substrate holding portion 116a, and as shown in FIG. 21, when the moving table 116 moves to the drainage area 150, the tilting cam 151 comes into abutment with the stopper 152 attached to the end portion of the guide device 117. Then, as shown in FIG. 22, when the moving table 116 is further moved to the stopper 152 side, the tilting cam 151 pivots about the pivot shaft 155, and the roller 154 attached to the distal end of the tilting cam 151 moves in such a way as to be lifted up. This movement of the roller 154 causes the substrate holding portion 116a to be lifted up with the rotary shaft 153 as a fulcrum as shown in FIG. 19. Thus, since the roller 154 is attached to the distal end of the tilting cam 151, it becomes possible to smoothly tilt the substrate holding portion 116a. Moreover, when the drainage is finished, while the moving table 116 is moved to a detection area 160 to be described later, since at this time, the abutment between the stopper 152 and the tilting cam 151 is released, the tilting of the substrate holding portion 116a is also released at the same time, and thus, the upper surface of the moving table 116 and the substrate holding portion 116a return to a substantially horizontal state.

Next, the moving table 116 is moved to the detection area 160 as shown in FIG. 23. The detection area 160 includes a detection camera 161, a moving mechanism 165 that moves the detection camera 161 up and down in a direction substantially perpendicular to the guide device 117, and a first cylinder 164 and a second cylinder 163 that move up and down together with the detection camera 161. A light shielding portion 162 is attached to the distal end of the second cylinder 163 and can cover the reaction area 11 so as to shield the injection hole 31 of the biochemical reaction substrate 1 from light when the detection camera 161 is moved to the lower end by the moving mechanism 165. Further, the first cylinder 164 is attached with the detection camera 161 at the upper end, and is fitted to the second cylinder 163. The fitting portion between the first cylinder 164 and the second cylinder 163 is assembled so as to be shielded from light via an O-ring (not shown) and the like, and held together by the elastic force of the O-ring. Note that the first cylinder 164 and the second cylinder 163 include an adjustment mechanism that allows them to be movable relative to each other to adjust the distance for focusing between the reaction area 11 of the biochemical reaction substrate 1 and the detection camera 161 when the detection camera 161 is lowered, and this adjustment mechanism is configured with the O-ring described above interposed therebetween. As described above, since the adjustment mechanism is configured such that the first cylinder 164 and the second cylinder 163 are attached to each other via the O-ring, the second cylinder 163 slides up and down on the contact surface of the O-ring, and thus can move up and down with respect to the first cylinder 164.

In this manner, in the detection area 160, after the drainage of the specimen or the like is finished, as shown in FIG. 23, the detection camera 161 is lowered, and the light shielding portion 162 provided at the distal end thereof is brought into close contact with the biochemical reaction substrate 1 to perform light shielding such that no outside light enters from the outside of the biochemical reaction substrate 1 and the analyzer 101. In this state, it is possible to detect the presence or absence of an allergic reaction by detecting the presence or absence of light emission of the labeled antibody after an elapse of a predetermined reaction time. Since a luminescent substrate which causes an labeled anti-IgE antibody to emit light and to be visualized has been dispensed as a reagent (reaction reagent), the light emission of the labeled antibody is performed by subjecting the luminescent substrate to biochemical reaction in the reaction area under a predetermined environmental condition for a predetermined time period, and the intensity of the emitted light is measured by the detection camera 161.

In this way, by configuring the dispensing nozzle 131 and the detection camera 161 to be able to move up and down together with the second cylinder 163, the first cylinder 164, and the light shielding portion 162, and by making the position of the biochemical reaction substrate 1 movable, it becomes possible to prevent the cover and the moving mechanism from becoming larger than a mechanism that moves the light shielding portion and the cover while the detection camera 161 is fixed, thereby contributing to the overall downsizing of the analyzer 101. Properly speaking, although it is desirable that the distance between the biochemical reaction substrate 1, in which a detection target is present, and the detection camera 161 is fixed to a certain distance to perform measurement accurately, when such a fixed scheme is adopted, it is necessary to move up and down the hood that constitutes a dark room structure so as to cover the detection camera and the biochemical reaction substrate 1 to shield light during measurement, resulting in upsizing of the hood. Further it is also necessary for the hood to shield light by covering the entire biochemical reaction substrate 1 and, to make such light shielding complete, a structure for causing the hood to come into close contact with a base on which the biochemical reaction substrate 1 is placed such as by attaching an elastic body to the bottom of the hood (non-movable) becomes necessary, and thus the analyzer 101 is difficult to be downsized. In contrast to this, the analyzer 101 according to the present embodiment moves the detection camera 161 itself up and down, and thereby suppresses the space of the dark room structure, enabling downsizing of the moving mechanism. Furthermore, since by arranging the second cylinder 163 inside the first cylinder 164, and attaching the light shielding portion 162 at the distal end thereof, thus bringing the light shielding portion 162 into close contact with biochemical reaction substrate 1, it becomes possible to shield the biochemical reaction substrate 1 from light, such light shielding becomes possible with a space a little larger than or substantially equivalent to cover the entire top plate area of the biochemical reaction substrate 1, or with a smaller space sufficient to cover the injection hole 31, and thus the moving mechanism can be downsized. Further, while moving mechanisms in various directions are required in the analyzer, such as for moving the dispensing nozzle 131, tilting the substrate holding portion 116a, and moving the barcode reader 121 and the like in accordance with the biochemical reaction substrate 1, providing a moving mechanism corresponding to each moving direction leads to an increase in the size of the analyzer. In contrast to this, the analyzer 101 according to the present embodiment achieves downsizing of the analyzer 101 by arranging the installation area 110, the dispensing area 130, the stirring area 140, the drainage area 150, and the detection area 160 in the same straight line, and integrating the moving mechanism of the biochemical reaction substrate 1 that moves between each areas into one axis.

According to such an analyzer, it is possible, in an allergy test, to achieve higher test sensitivity and shorter testing time, reduce a required amount of blood or the like needed as the specimen, and decrease the number of test steps, thereby facilitating performance of the test, and it is also possible to reduce the risk of infection of the test staff, and to perform all the steps by moving on only one axis by disposing the installation area, the dispensing area, the stirring area, the drainage area, and the detection area on the same straight line, thus enabling downsizing of the entire apparatus.

EXAMPLE

Next, detection results of the analyzer 101 according to the present embodiment will be described with reference to FIGS. 24 to 27. As shown in FIG. 24, in the present example, test was carried out by arranging antigens A (Cockroach), B (Timothy) and C (Salmon) in the reaction area of the biochemical reaction substrate.

As shown in FIG. 25, in a state in which 60 seconds of exposure had elapsed after stirring, the antigen A and the antigen B were emitting light, and the light emission was confirmed by the detection camera. In addition, regarding the antigen C, strong light emission was not confirmed, and it was confirmed that this specimen contained a minute amount of IgE antibody with respect to the antigen C.

Moreover, it was confirmed that light emission due to remaining drainage around the reaction area was suppressed. Note that, although some light emission was confirmed around the reaction area, it was also confirmed that the light emission was in a range that did not affect the analysis, and did not affect the detection performance of the analyzer.

Note that regarding the antigen B, the light emission was strong when the exposure time was 60 seconds. On the other hand, as shown in FIGS. 25 to 27, the analyzer 101 according to the present embodiment performed photographing at intervals of exposure time of 5 seconds, 20 seconds, and 60 seconds. From the result, while the light emission of antigen B strongly affected the detection performance after elapse of 60 seconds, when the exposure time was 20 seconds, the light emission of the antigen B was in a state of appropriate intensity as shown in FIG. 26, the detection performance for the antigen B was ensured by using a detection result with an exposure time of 20 seconds. Furthermore, in the analyzer 101 in the present embodiment, although a state of exposure time of 5 seconds was also photographed as shown in FIG. 27, for the antigens A to C of this time, the light emission was feeble in 5 seconds. However, for antigens with strong light emission, the detection performance of the analyzer 101 can be further improved by using a detection result with an exposure time of 5 seconds.

Note that although the biochemical reaction substrate 1 according to the above-described embodiment has been described on cases where the injection hole 31 and the reaction area 11 are formed into a circle, these shapes are not limited to a circle and can be formed into, for example, an elliptical shape.

Moreover, as the reaction plate 10 used for the biochemical reaction substrate 1 according to the present embodiment described above, a transparent or colored plate can be used, but by using black, it is possible to measure at higher sensitivity. Moreover, by setting the range of the blocking agent applied to the reaction plate 10 to the reaction area 11 including the inside of the flow-out prevention wall 13 and the slope 15, as well as to the inside of the flow passage 12, it is possible to suppress further non-specific adsorption.

Further, although the tilting direction by the tilting mechanism used in the analyzer 101 according to the present embodiment has been described with reference to FIG. 19, it is not limited to tilting in a direction perpendicular to the guide device 117, and it may be tilted, for example, in the horizontal direction with respect to the guide device 117 depending on the position of the tilting cam 151 or the position of the rotary shaft 153. Furthermore, the reagent cartridge 113 may be one in which all the reagents and specimens used for measurement are collected, or two or more reagent cartridges may be used depending on the application. It is apparent from the description of claims that embodiments with such changes or improvements can be included in the technical scope of the present invention.

REFERENCE SIGNS LIST

1 Biochemical reaction substrate,
10 Reaction plate,
11 Reaction area,

12 Flow passage,
13 Flow-out prevention wall,
14 Base portion,
15 Slope,
20 Absorber,
30 Cover,
31 Injection hole,
32 Inner wall portion,
33 Missing portion for suction prevention,
34 Missing portion for adjustment,
35 Slip prevention device,
36 Top side,
37 Defining wall,
38, 45 Rib,
40 Storage container,
41 Reaction plate storing portion,
42 Absorber storing portion,
43 Heated portion,
44 Storage portion groove,
46 Opening portion,
50 Antigen,
51 Set,
101 Analyzer,
102 Operating section,
103 Loading section,
104 Housing,
110 Installation area,
111 Specimen,
112a Reaction reagent,
112b Cleaning solution,
113 Reagent cartridge,
115 Heating section,
116 Moving table,
116a Substrate holding portion,
117 Guide device,
118 Driving section,
120 Barcode reading area,
121 Barcode reader,
130 Dispensing area,
131 Dispensing nozzle,
132 Chip,
140 Stirring area,
150 Drainage area,
151 Tilting cam,
152 Stopper,
153 Rotary shaft,
154 Roller,
155 Pivot shaft,
160 Detection area,
161 Detection camera,
162 Light shielding portion,
163 Second cylinder,
164 First cylinder,
165 Moving mechanism.

The invention claimed is:

1. A biochemical reaction substrate, comprising:
a reaction plate; an absorber; a reaction plate storing portion for storing the reaction plate; an absorber storing portion for storing the absorber; a storage container having a wall; and a cover assembled to the storage container so as to cover at least a part of the reaction plate and the absorber stored in the storage container, wherein
the reaction plate includes a reaction area in which a specific binding substance that specifically reacts with a substance to be tested in a specimen is immobilized, and a flow passage that connects the absorber and the reaction area, and wherein
the cover includes an injection hole for injecting a specimen or the like into the reaction plate,
wherein the reaction plate storing portion and the absorber storing portion are in the storage container, and
wherein the flow passage has a slope formed in such a way to climb up from the reaction area.

2. The biochemical reaction substrate according to claim 1, wherein
the reaction plate comprises a flow-out prevention wall along at least part of the flow passage and at least partly surrounding the reaction area.

3. The biochemical reaction substrate according to claim 2, wherein
the cover includes an inner wall portion abutting the reaction plate along at least a part of an outer peripheral edge of the flow-out prevention wall.

4. The biochemical reaction substrate according to claim 3,
the inner wall portion has a missing portion which is a gap for suction prevention in the inner wall portion and adjacent to the flow passage, and the reaction plate storing portion has a storage portion groove formed to be continuous with the absorber storing portion.

5. An analyzer for analyzing reaction between a specimen and a reagent, the analyzer comprising:
an installation area comprising therein a reagent cartridge, for storing the specimen and the reagent, and a biochemical reaction substrate for dispensing the specimen and the reagent;
a dispensing area where the specimen and/or the reagent is dispensed into the biochemical reaction substrate;
a stirring area where the dispensed specimen and/or reagent is stirred and mixed;
a drainage area where the stirred and mixed specimen and reagent are drained;
a detection area where reaction between the specimen and the reagent in the biochemical reaction substrate is detected, wherein the installation area, the dispensing area, the stirring area, the drainage area and the detection area are, in any order, arranged on a same straight line;
a guide device disposed along the same straight line and comprising a drive source; and
a moving table guided, by the drive source along the guide device, among each the installation area, the dispensing area, the stirring area, the drainage area and the detection area.

6. The analyzer according to claim 5, wherein
the installation area is disposed at a first end portion of the same straight line, and
the drainage area is disposed at a second end portion of the same straight line, the second end portion being at an opposite end of the same straight line than the first end portion.

7. The analyzer according to claim 5, wherein
the moving table is oscillated in the stirring area by reciprocally moving the moving table along the same straight line.

8. The analyzer according to claim 5, wherein
the dispensing area comprises a dispensing nozzle which is movable in a direction substantially perpendicular to the same straight line.

9. The analyzer according to claim 5, wherein
the moving table comprises a substrate holding part in which the biochemical reaction substrate is arranged, and
the drainage area comprises a tilting mechanism which includes a stopper formed at an end portion of the same straight line, and causes the substrate holding part to abut against the stopper and to be tilted.

10. The analyzer according to claim 5, wherein
the detection area includes a light shielding portion for shielding the biochemical reaction substrate from light, and a detection camera for detecting the biochemical reaction substrate surface, and
the detection camera includes a moving mechanism that allows the detection camera to move in a direction substantially perpendicular to the same straight line.

11. The analyzer according to claim 10, wherein
the light shielding portion includes an adjustment mechanism that is moved along with the detection camera by the moving mechanism, and can adjust the distance of an end portion of the light shielding portion from the detection camera.

12. The analyzer according to claim 11, wherein
the adjustment mechanism comprises a first cylinder at one end of which the detection camera is attached, and a second cylinder attached to a second end the first cylinder, the second end is opposite to the one end.

* * * * *